US010222612B2

(12) United States Patent
Okada et al.

(10) Patent No.: US 10,222,612 B2
(45) Date of Patent: Mar. 5, 2019

(54) OPTICAL DEVICE, PHASE PLATE, AND IMAGE FORMING METHOD

(71) Applicant: Sysmex Corporation, Kobe-shi, Hyogo (JP)

(72) Inventors: Masaya Okada, Kobe (JP); Shigeki Iwanaga, Kobe (JP)

(73) Assignee: SYSMEX CORPORATION, Kobe-Shi, Hyogo (JP)

( * ) Notice: Subject to any disclaimer, the term of this patent is extended or adjusted under 35 U.S.C. 154(b) by 0 days.

(21) Appl. No.: 15/454,505

(22) Filed: Mar. 9, 2017

(65) Prior Publication Data

US 2017/0261744 A1 Sep. 14, 2017

(30) Foreign Application Priority Data

Mar. 10, 2016 (JP) .................................. 2016-047682

(51) Int. Cl.
  *G02B 27/00* (2006.01)
  *G01N 21/64* (2006.01)
  *G02B 21/00* (2006.01)

(52) U.S. Cl.
  CPC ..... *G02B 27/0068* (2013.01); *G01N 21/6458* (2013.01); *G02B 21/0056* (2013.01); *G02B 21/0064* (2013.01); *G02B 21/0076* (2013.01)

(58) Field of Classification Search
  CPC ............ G02B 27/0068; G02B 21/0056; G02B 21/0076; G01N 21/6458
  USPC .................................................. 359/370, 386
  See application file for complete search history.

(56) References Cited

U.S. PATENT DOCUMENTS

| 5,291,012 | A | 3/1994 | Shimizu et al. | |
|---|---|---|---|---|
| 7,609,391 | B2 * | 10/2009 | Betzig | G01N 21/6445 356/457 |
| 9,911,180 | B2 * | 3/2018 | Crowe | G06T 5/003 |
| 9,927,300 | B2 * | 3/2018 | Golub | G01J 3/2823 |
| 9,940,694 | B2 * | 4/2018 | Isoyan | G06T 3/40 |
| 9,946,081 | B2 * | 4/2018 | Arnold | G02B 27/0927 |

(Continued)

FOREIGN PATENT DOCUMENTS

| DE | 42 14 069 A1 | 11/1992 |
|---|---|---|
| JP | 2010-025922 A | 2/2010 |

(Continued)

OTHER PUBLICATIONS

Ashok et al., "Pseudorandom phase masks for superresolution imaging frm subpixel shifting", Applied Optics, vol. 46, No. 12, Apr. 20, 2007.*

(Continued)

*Primary Examiner* — Frank G Font
(74) *Attorney, Agent, or Firm* — Brinks Gilson & Lione

(57) ABSTRACT

An optical device comprises a shared phase modulation mask configured to impart a first phase modulation to light of a first wavelength, and imparts a second phase modulation to light of a second wavelength, an irradiation optical system configured to cause the light of the first wavelength and the light of the second wavelength to enter the same incident region in the phase modulation mask, and a light collecting optical system configured to collect the light of the first phase-modulated first wavelength and the light of the second phase-modulated second wavelength to form an image corresponding to a point spread function.

15 Claims, 30 Drawing Sheets

(56) References Cited

U.S. PATENT DOCUMENTS 10,026,011 B2 * 7/2018 Tsuchiya .............. G06K 9/6218
2001/0045529 A1   11/2001 Iketaki et al.
2010/0278400 A1   11/2010 Piestun et al.

FOREIGN PATENT DOCUMENTS

| JP | 2013-200374 A | 10/2013 |
| JP | 2013-225118 A | 10/2013 |
| JP | 2014-164004 A | 9/2014 |
| JP | 2014-182239 A | 9/2014 |
| JP | 2015-225120 A | 12/2015 |

OTHER PUBLICATIONS

Gahlmann, A. et al., "Quantitative Multicolor Subdiffraction Imaging of Bacterial Protein Ultrastructures in Three Dimensions", *NANO Letters—American Chemical Society*, vol. 13, 2013, pp. 987-993.

* cited by examiner

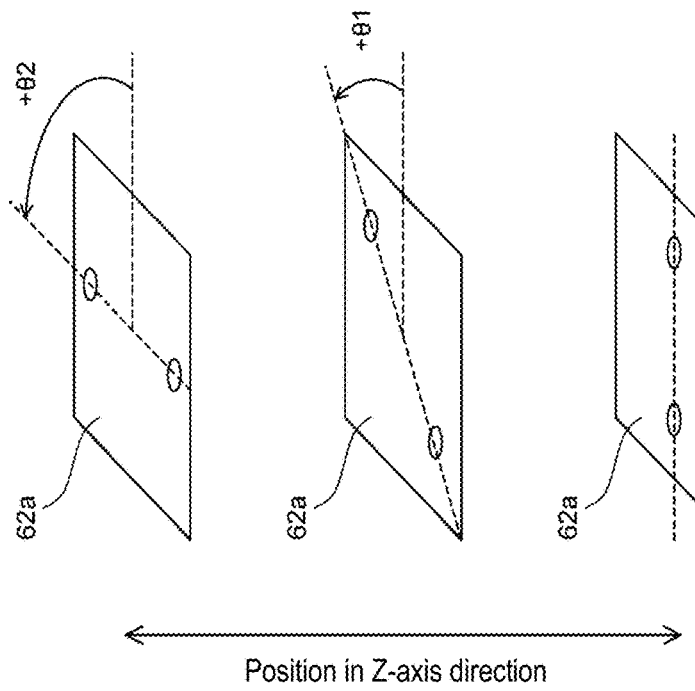

$$U(u,v) = A_1 \exp\left[\frac{-(u-\mu_{x1})^2}{2\sigma_{x1}^2}\right] \exp\left[\frac{-(v-\mu_{y1})^2}{2\sigma_{y1}^2}\right]$$
$$+ A_2 \exp\left[\frac{-(u-\mu_{x2})^2}{2\sigma_{x2}^2}\right] \exp\left[\frac{-(v-\mu_{y2})^2}{2\sigma_{y2}^2}\right] + B$$

$(u, v)$    Coordinates on Imaging surface
$A_1$    Brightness of bright spot 1
$A_2$    Brightness of bright spot 2
$(\mu_{x1}, \mu_{y1})$    Position of bright spot 1
$(\mu_{x2}, \mu_{y2})$    Position of bright spot 2
$\sigma_{x1}, \sigma_{y1}$    Size of bright spot 1
$\sigma_{x2}, \sigma_{y2}$    Size of bright spot 2
$B$    Brightness of background

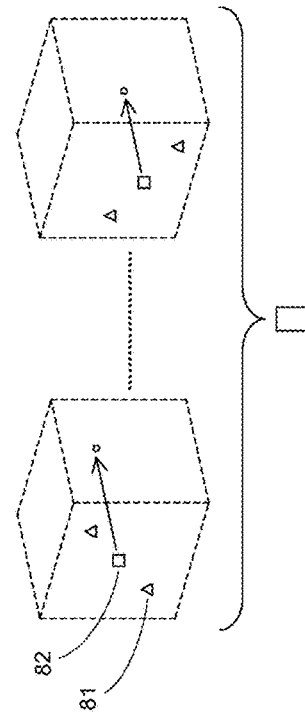
FIG. 4 (a)
FIG. 4 (b)
FIG. 4 (c)
FIG. 4 (d)
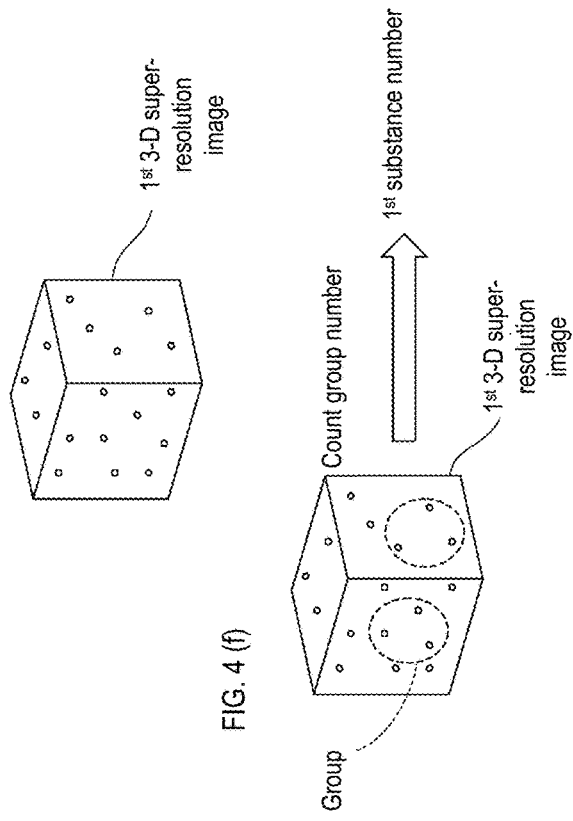
FIG. 4 (e)
FIG. 4 (f)

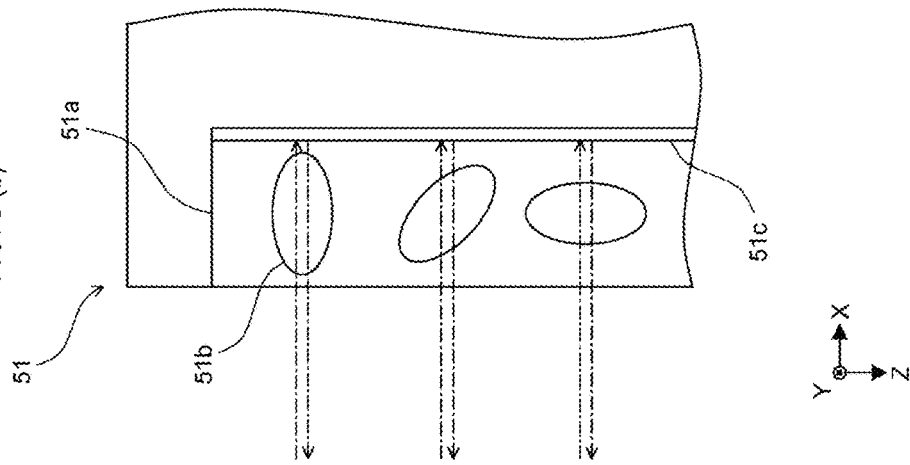
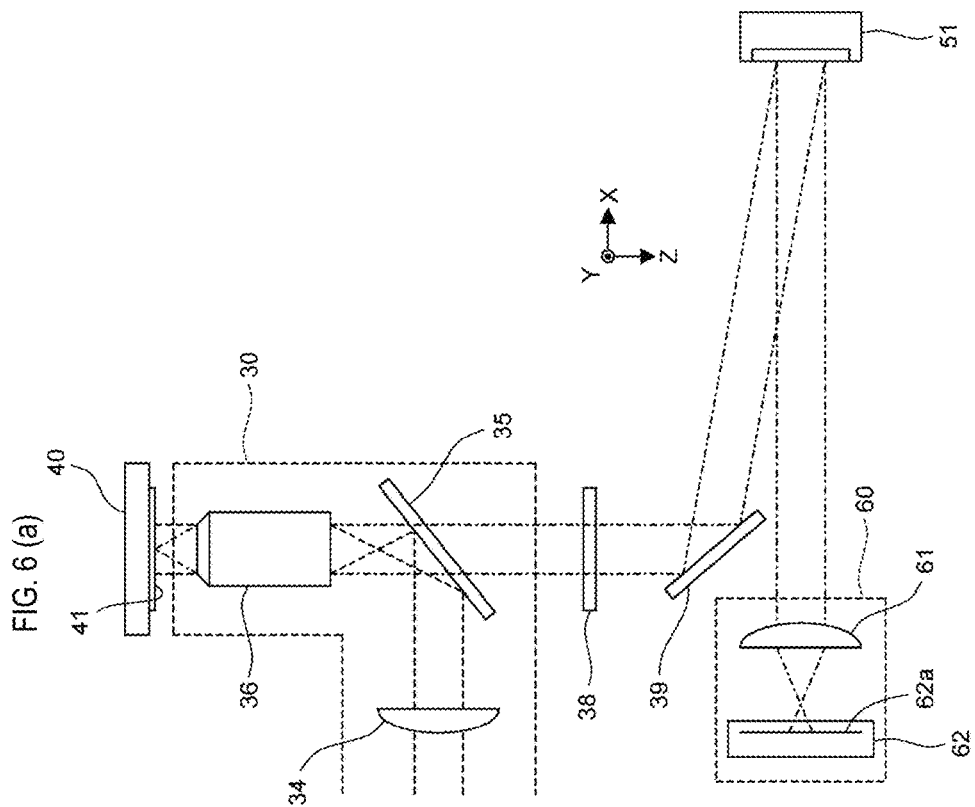

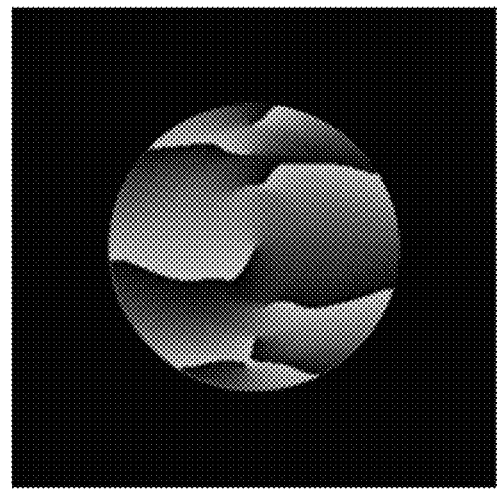
FIG. 7 (a) 1st phase modulation pattern
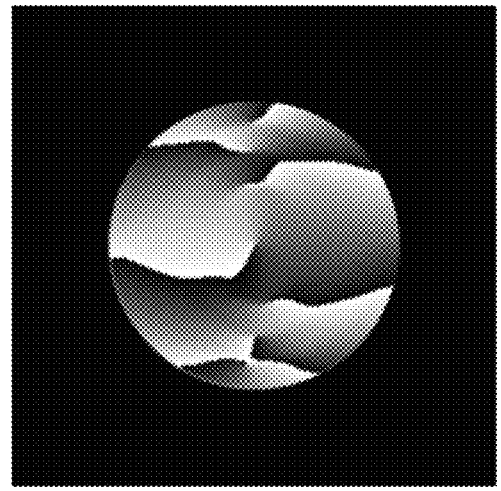
FIG. 7 (b) 2nd phase modulation pattern

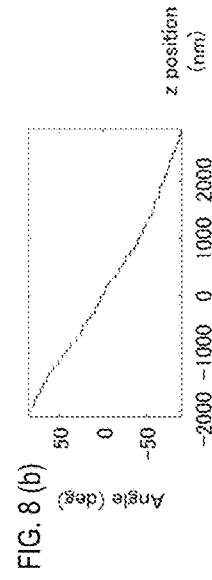
FIG. 8 (b)
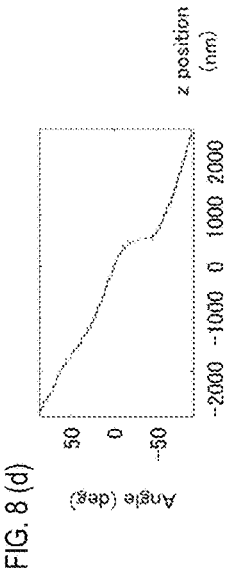
FIG. 8 (d)
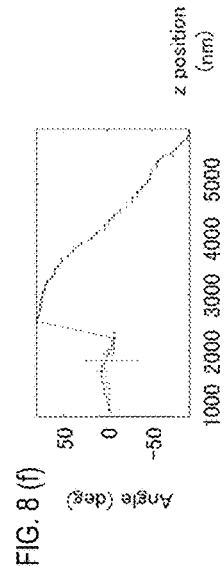
FIG. 8 (f)
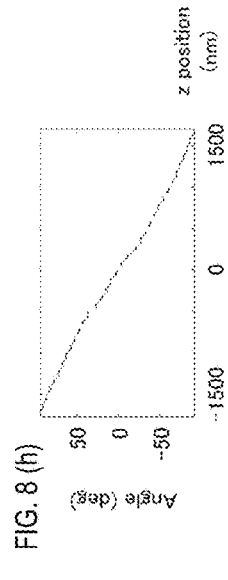
FIG. 8 (h)
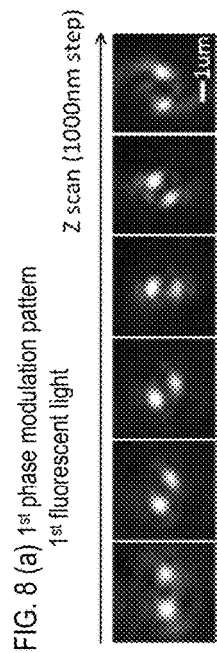
FIG. 8 (a) 1st phase modulation pattern
1st fluorescent light
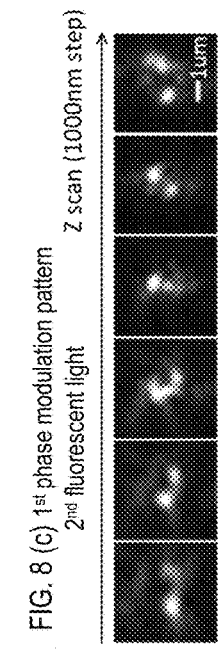
FIG. 8 (c) 1st phase modulation pattern
2nd fluorescent light
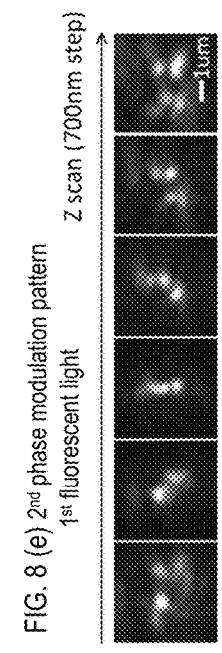
FIG. 8 (e) 2nd phase modulation pattern
1st fluorescent light
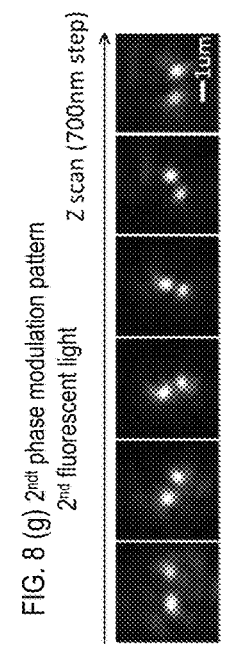
FIG. 8 (g) 2nd phase modulation pattern
2nd fluorescent light Phase modulation pattern example 1

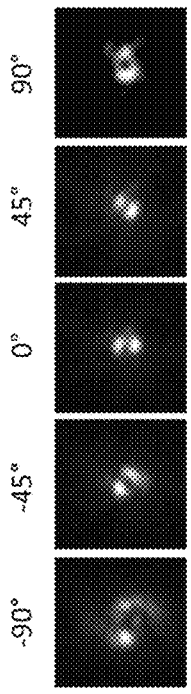
FIG. 12 (a)  a=5, b=5  1st fluorescent light
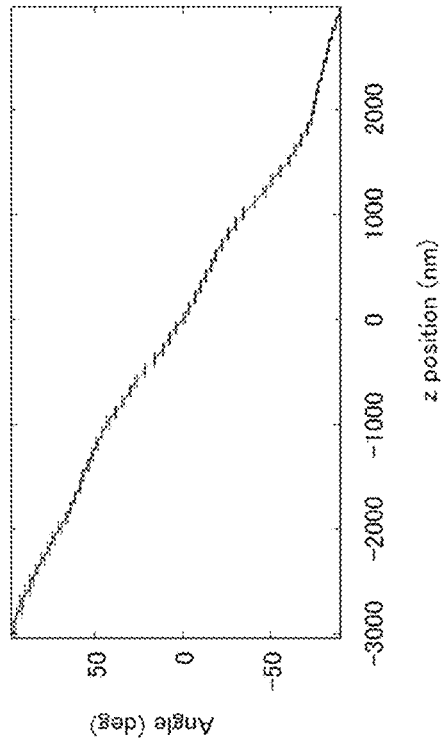
FIG. 12 (b)
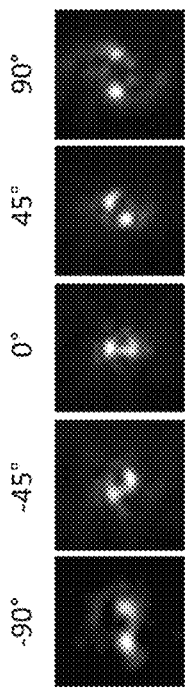
FIG. 12 (c)  a=5, b=5  2nd fluorescent light
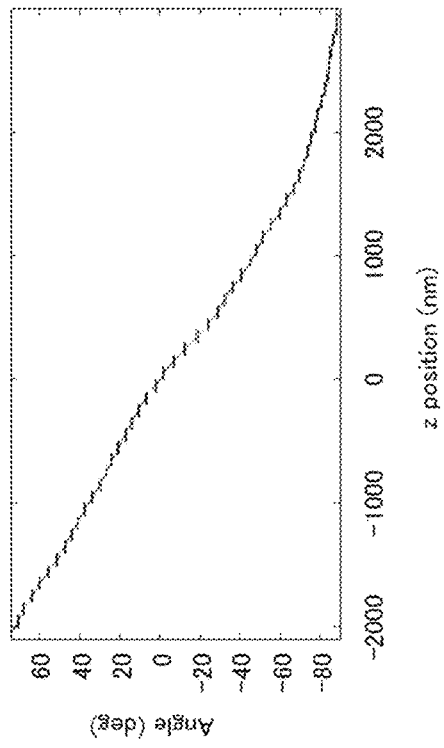
FIG. 12 (d)

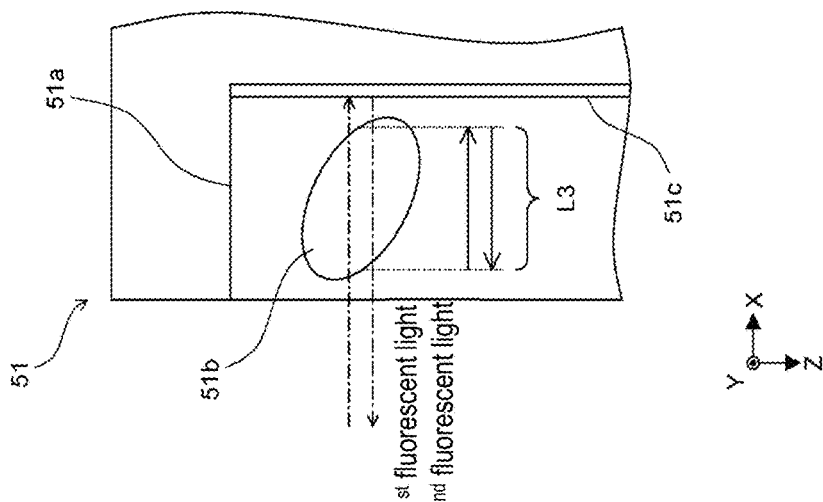
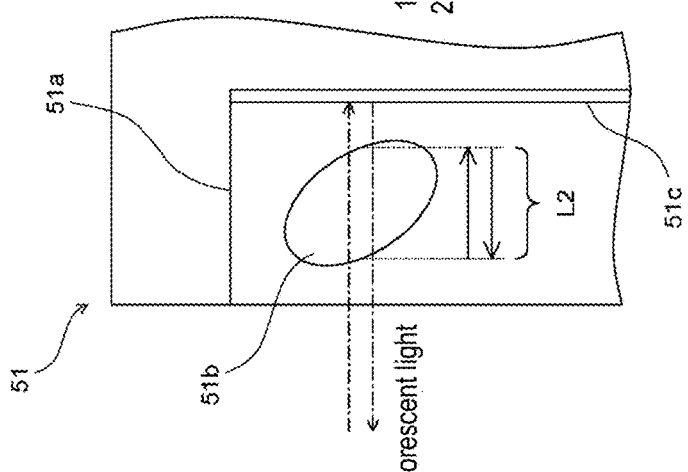
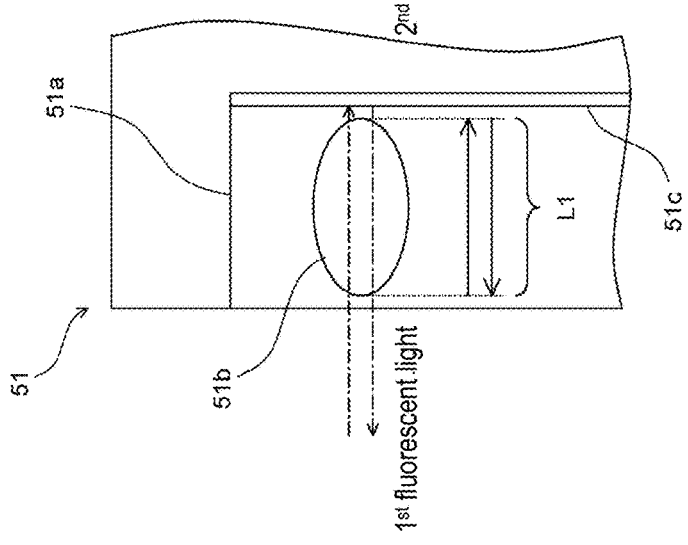

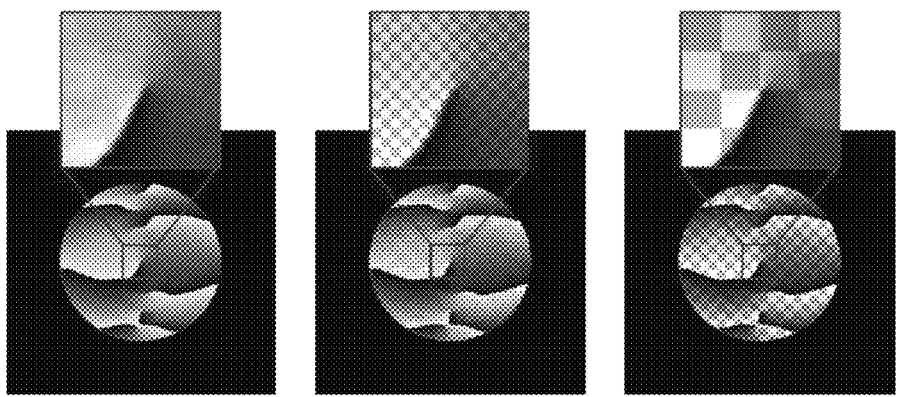
FIG. 14 (b) M=1
FIG. 14 (c) M=2
FIG. 14 (d) M=3
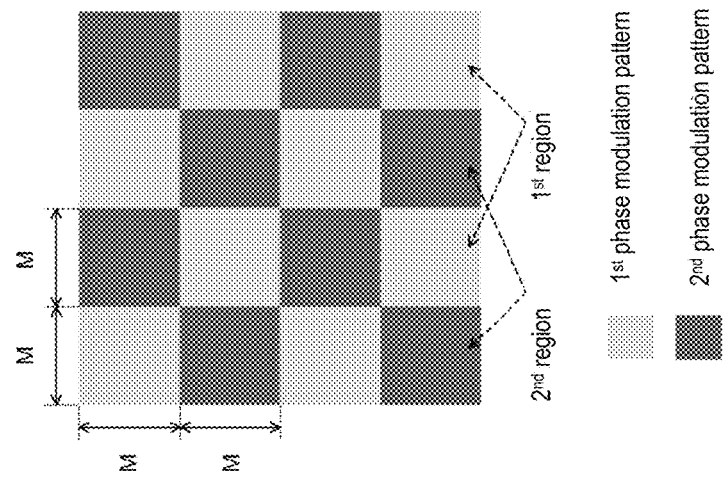
FIG. 14 (a) Phase modulation pattern example 2
1st region
2nd region
1st phase modulation pattern
2nd phase modulation pattern

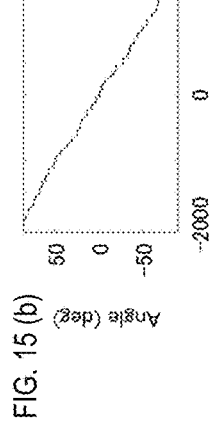
FIG. 15 (b)
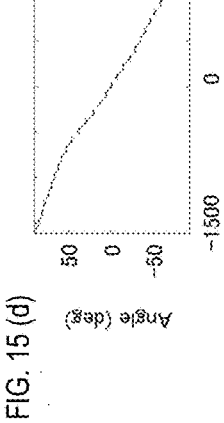
FIG. 15 (d)
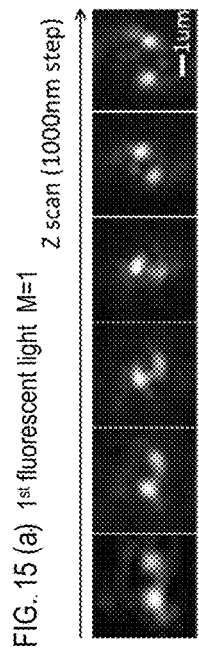
FIG. 15 (a) 1st fluorescent light M=1   Z scan (1000nm step)
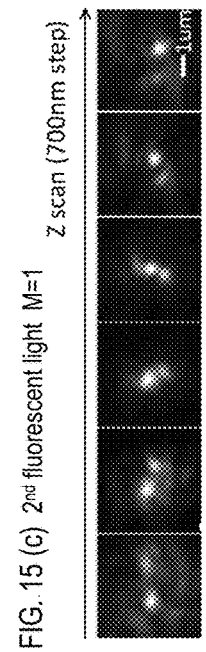
FIG. 15 (c) 2nd fluorescent light M=1   Z scan (700nm step)
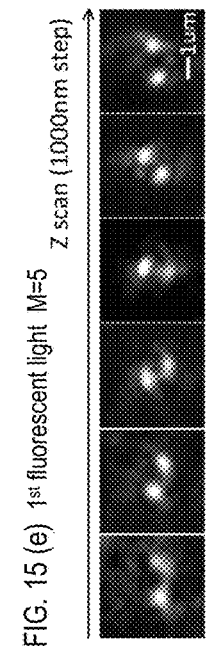
FIG. 15 (e) 1st fluorescent light M=5   Z scan (1000nm step)
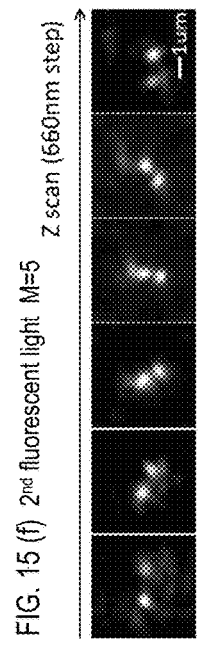
FIG. 15 (f) 2nd fluorescent light M=5   Z scan (660nm step)

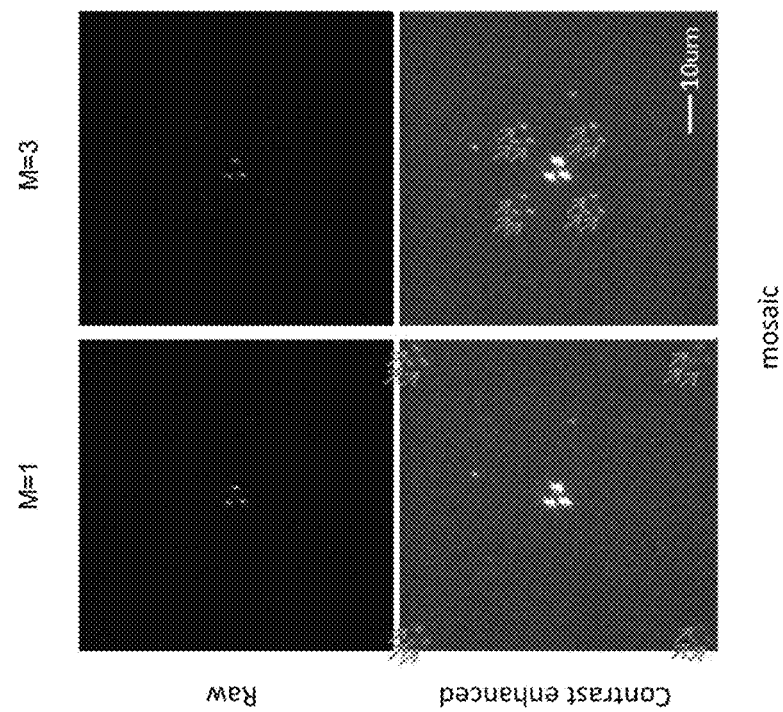
FIG. 16 (a) 1st fluorescent light
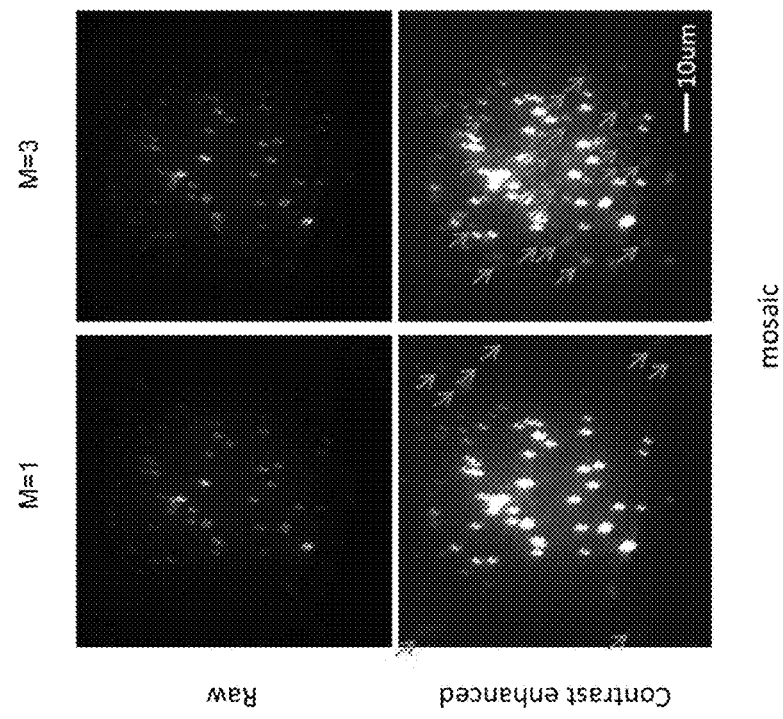
FIG. 16 (b) 2nd fluorescent light

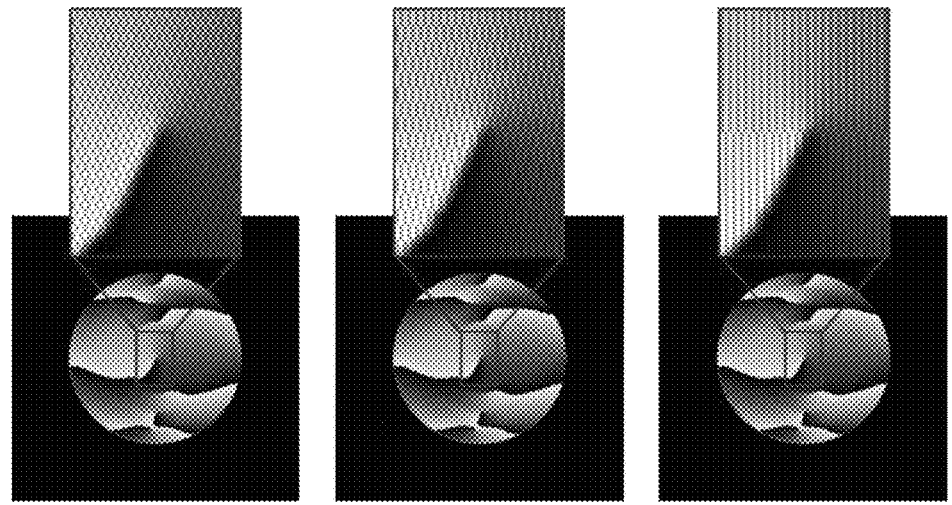
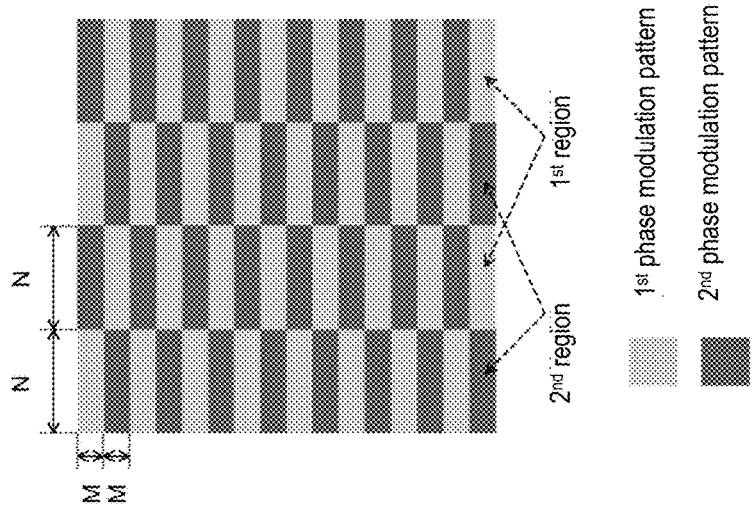

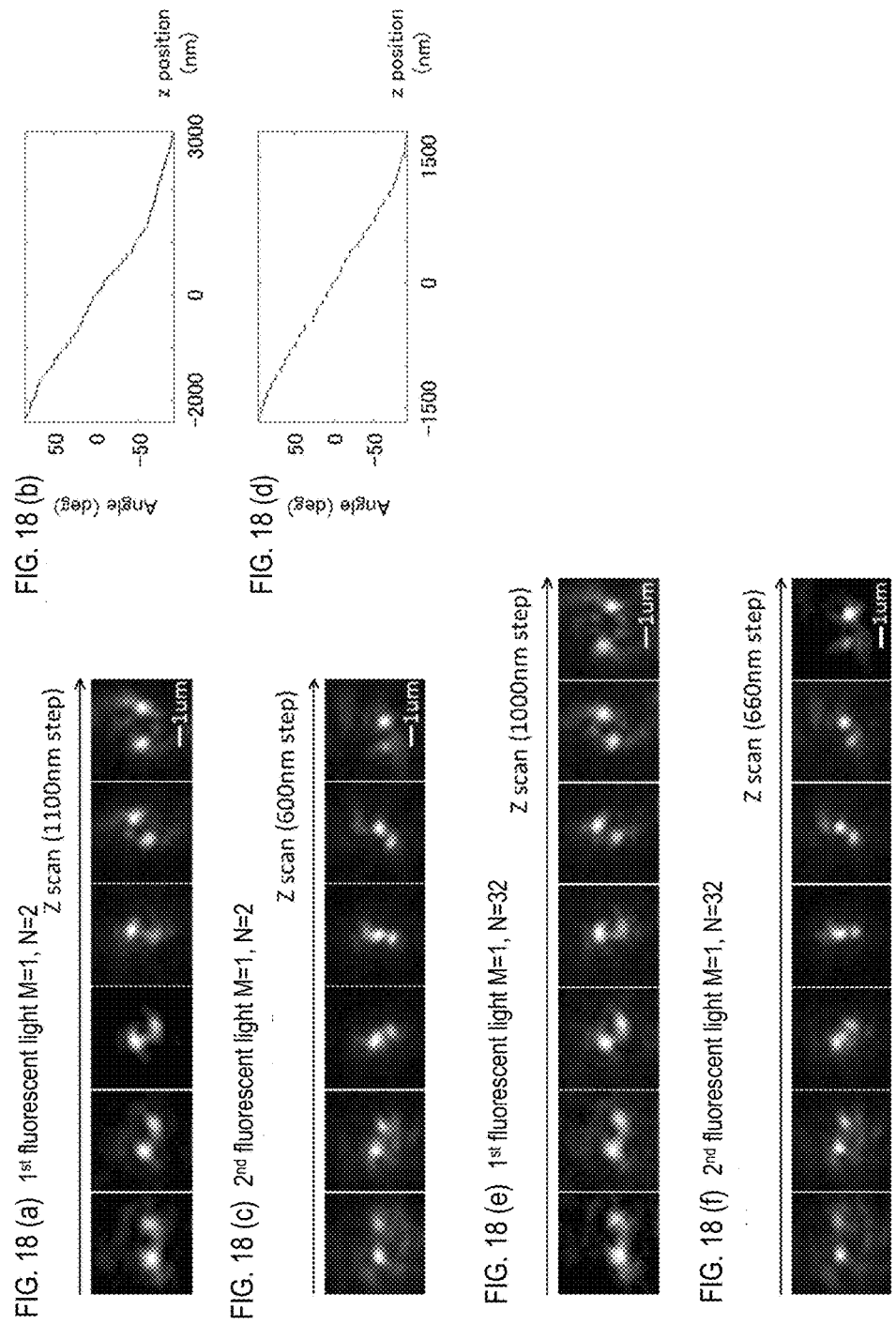

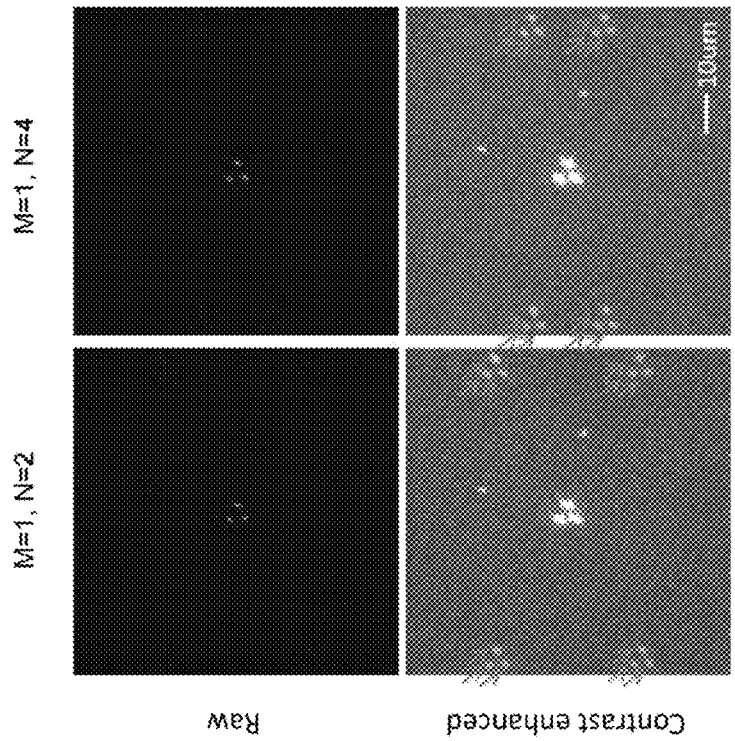
FIG. 19 (b)   2nd fluorescent light
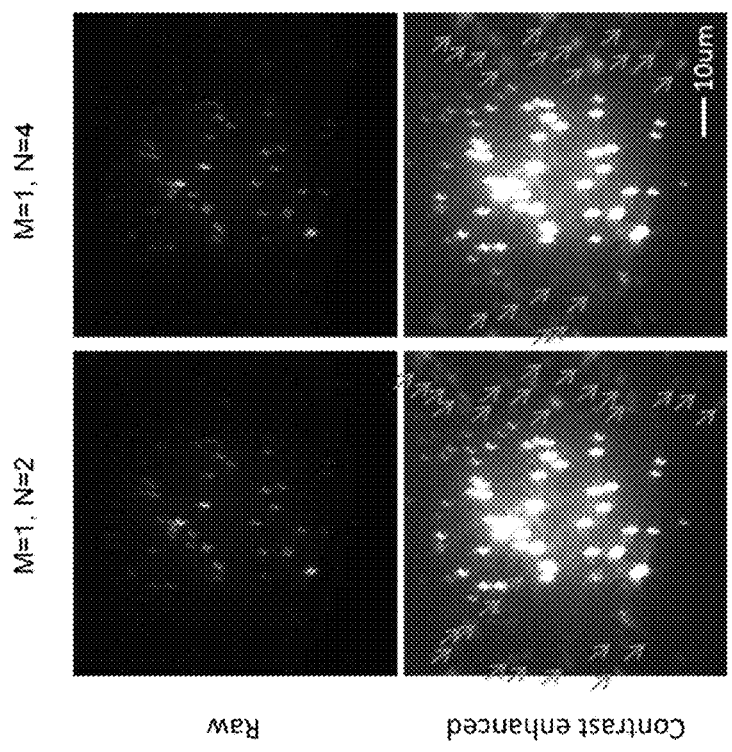
FIG. 19 (a)   1st fluorescent light

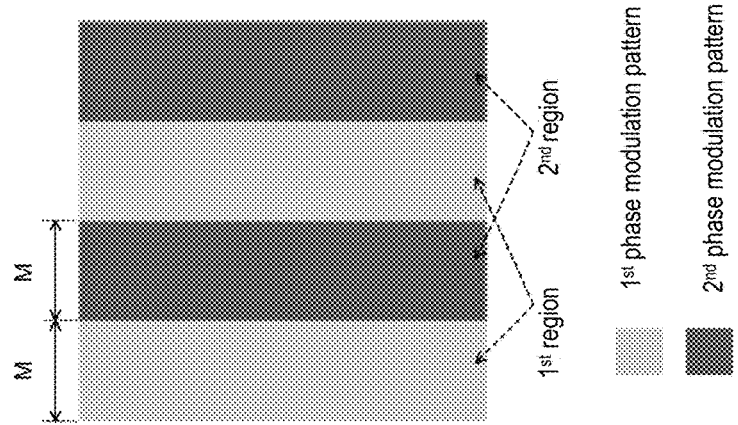
FIG. 20 (a)
Phase modulation pattern example 4
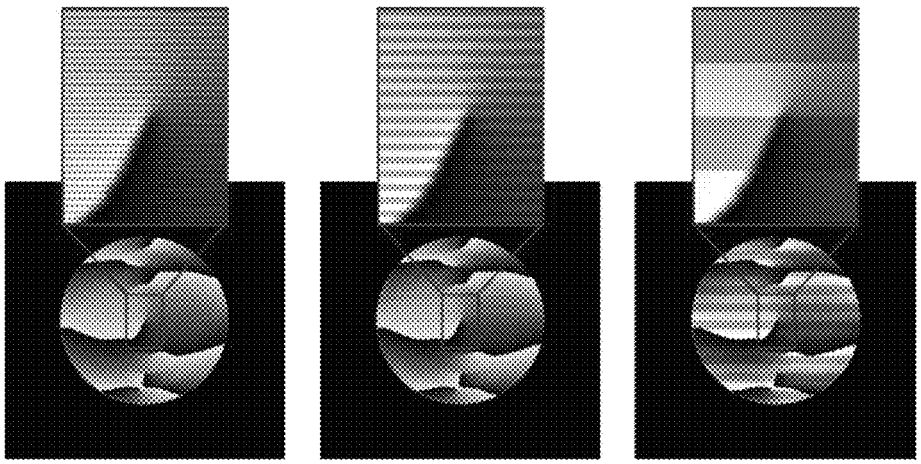
FIG. 20 (b)  M=1
FIG. 20 (c)  M=2
FIG. 20 (d)  M=16

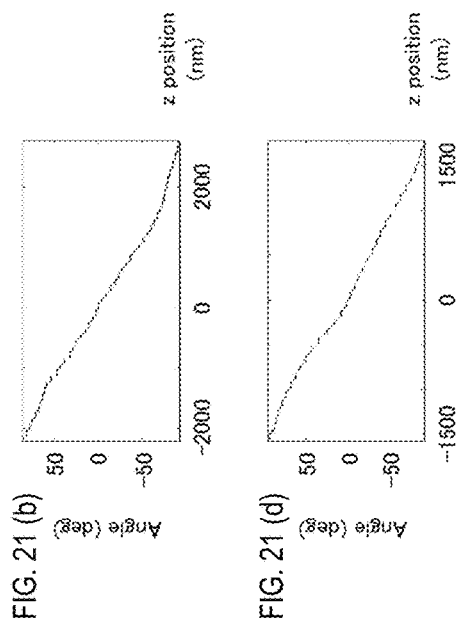
FIG. 21 (b)
FIG. 21 (d)
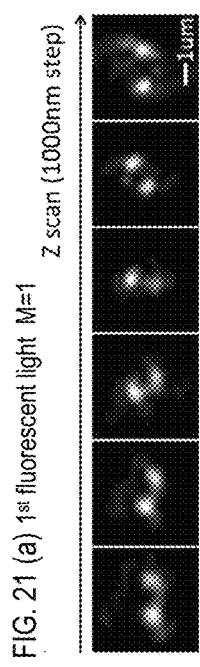
FIG. 21 (a) 1st fluorescent light M=1   Z scan (1000nm step)
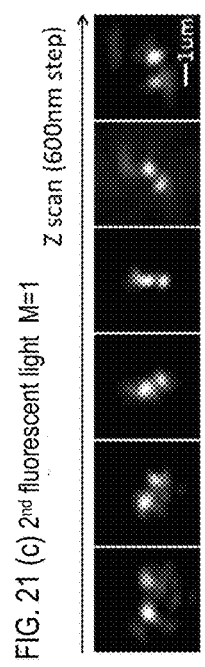
FIG. 21 (c) 2nd fluorescent light M=1   Z scan (600nm step)
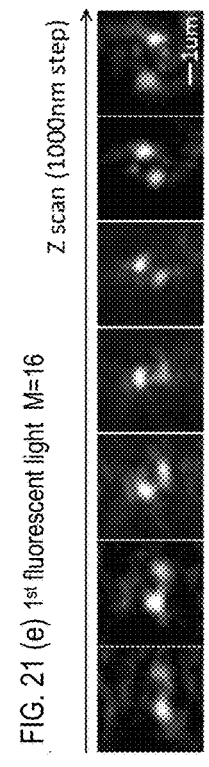
FIG. 21 (e) 1st fluorescent light M=16   Z scan (1000nm step)
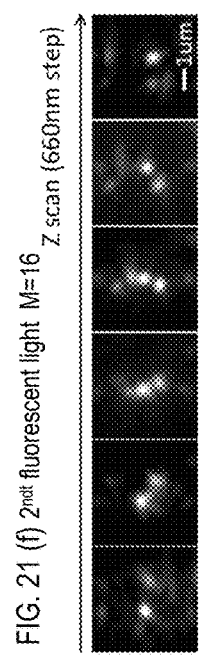
FIG. 21 (f) 2nd fluorescent light M=16   Z scan (660nm step)

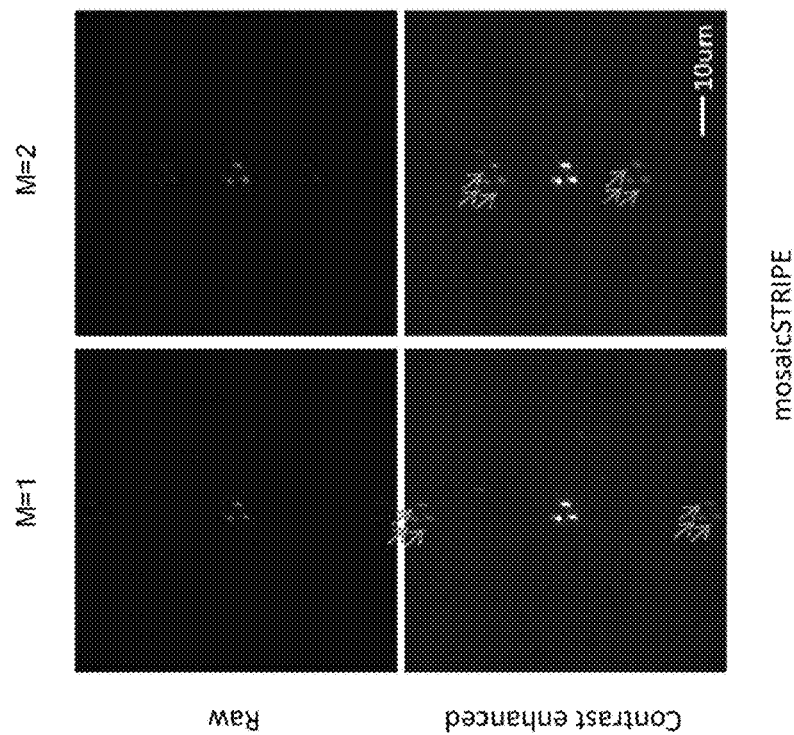
FIG. 22 (a) 1st fluorescent light
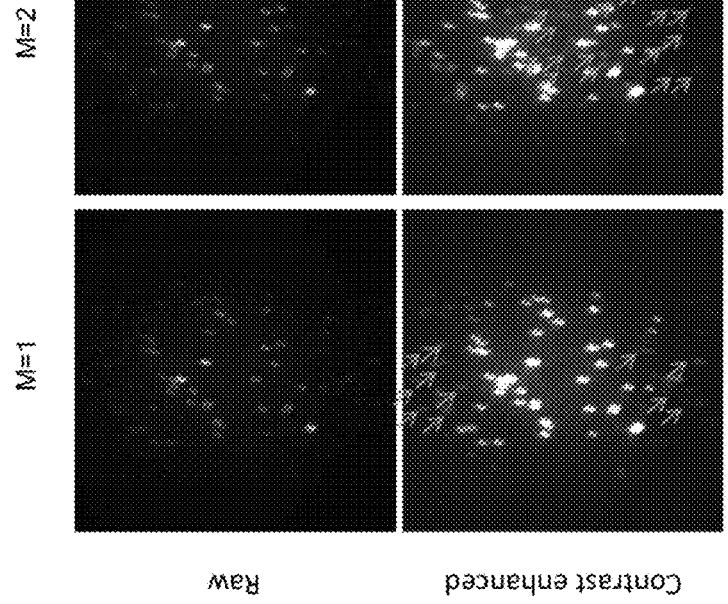
FIG. 22 (b) 2nd fluorescent light

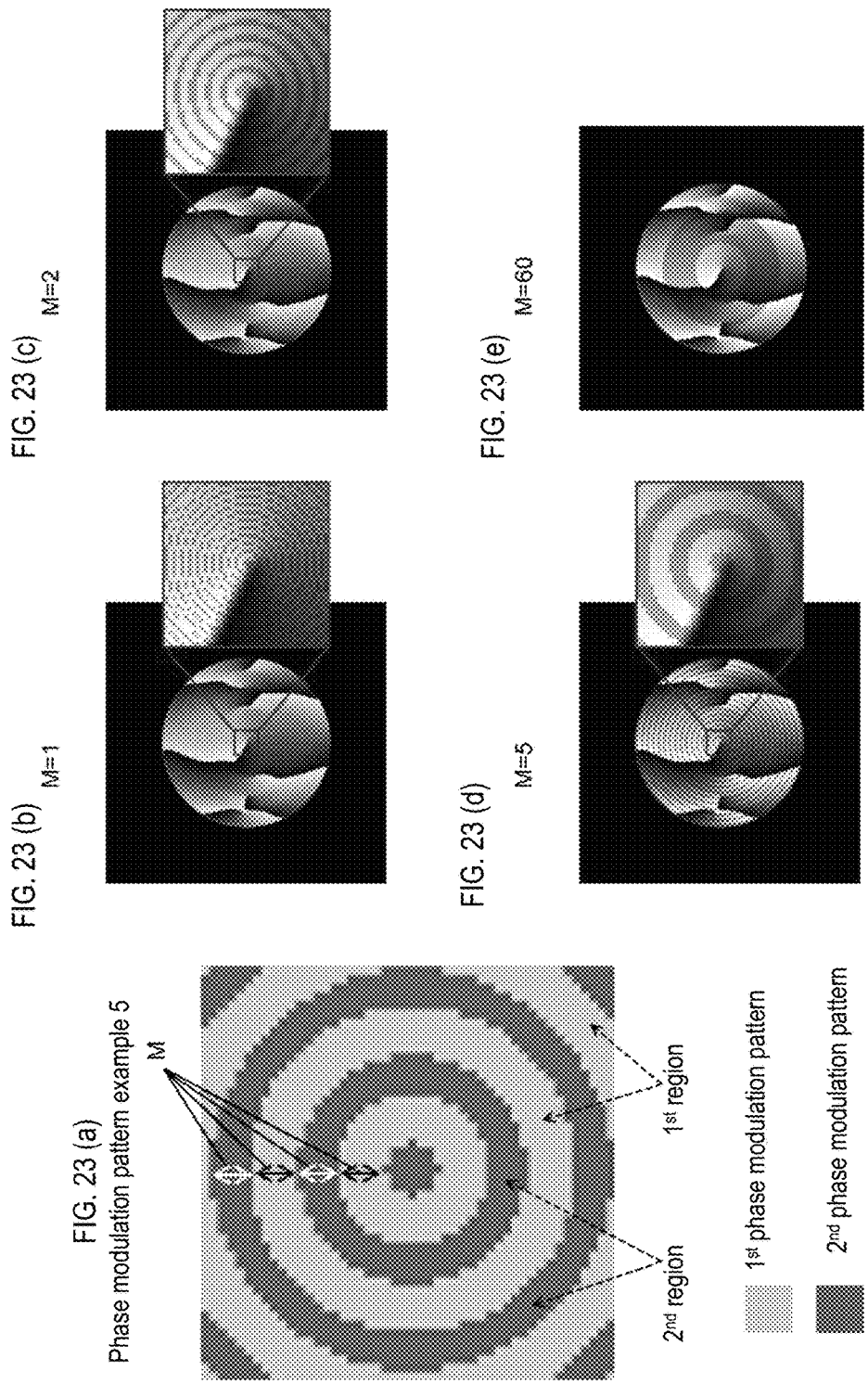

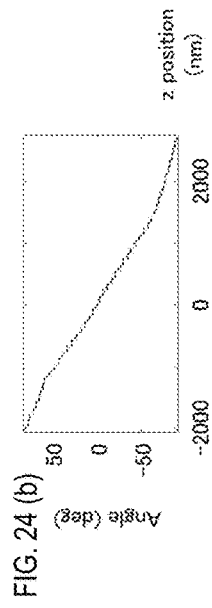
FIG. 24 (a) 1st fluorescent light M=1
Z scan (1000nm step)
FIG. 24 (b)
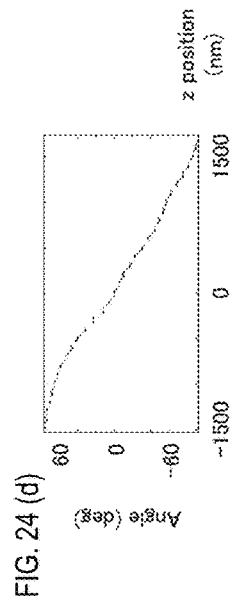
FIG. 24 (c) 2nd fluorescent light M=1
Z scan (600nm step)
FIG. 24 (d)
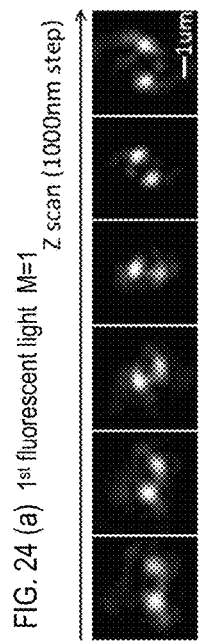
FIG. 24 (e) 1st fluorescent light M=5
Z scan (1000nm step)
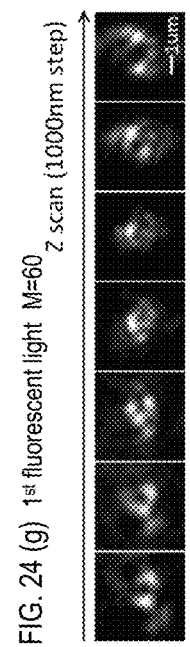
FIG. 24 (g) 1st fluorescent light M=60
Z scan (1000nm step)
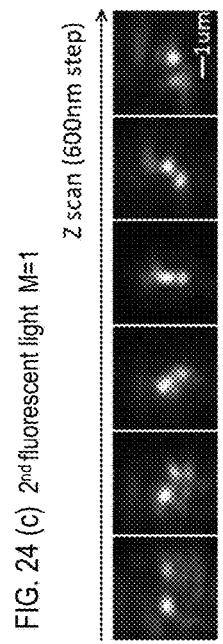
FIG. 24 (f) 2nd fluorescent light M=5
Z scan (660nm step)
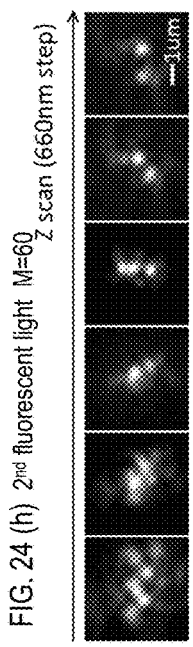
FIG. 24 (h) 2nd fluorescent light M=60
Z scan (660nm step)
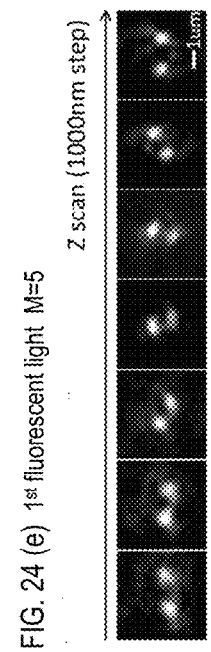
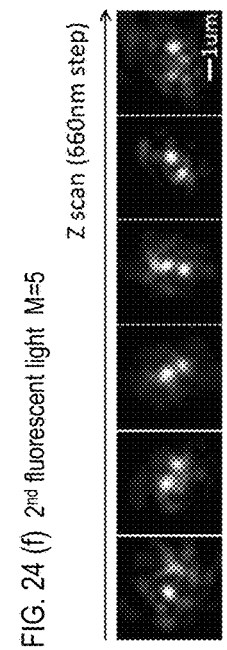

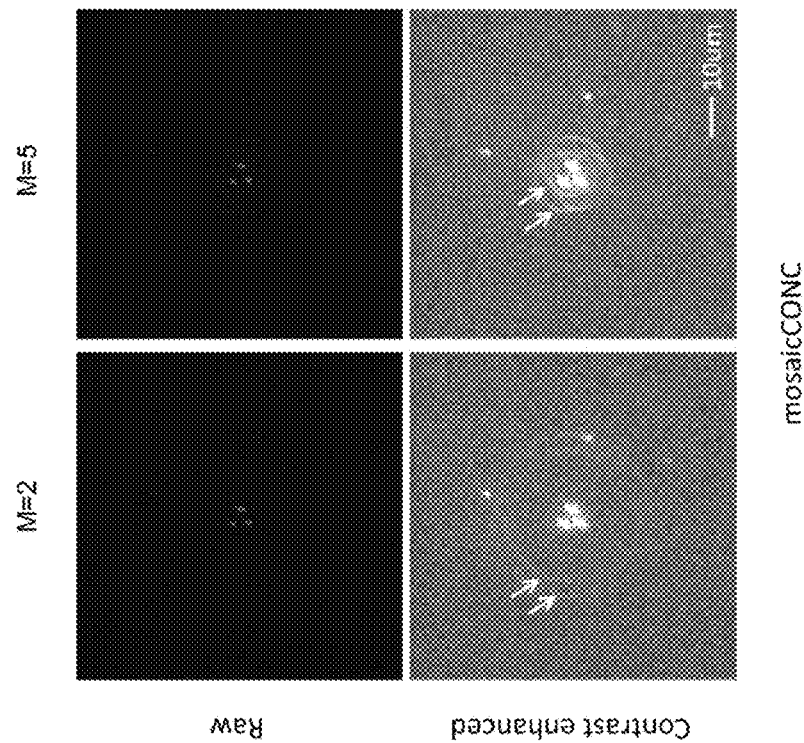
FIG. 25 (b) 2nd fluorescent light
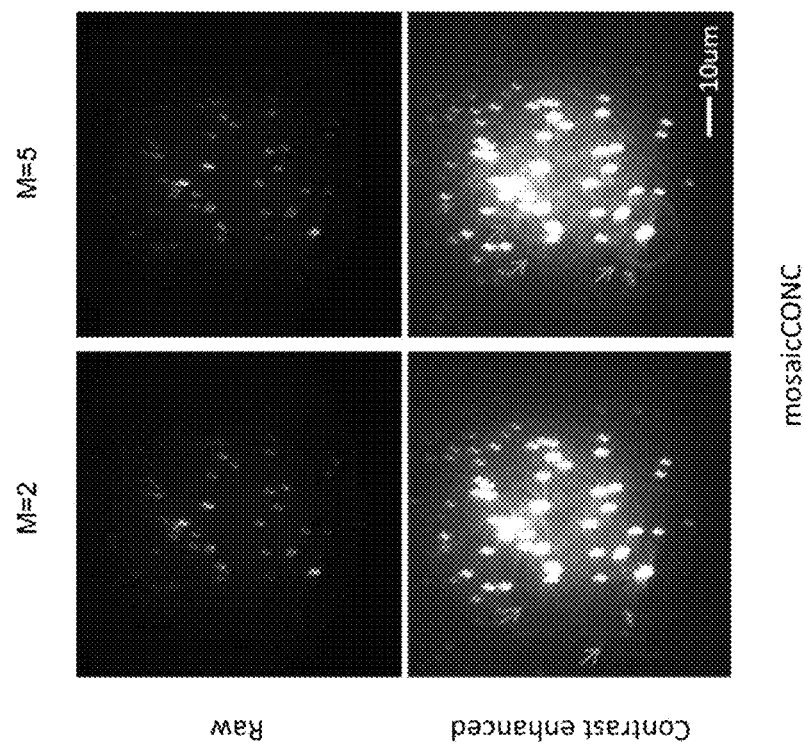
FIG. 25 (a) 1st fluorescent light

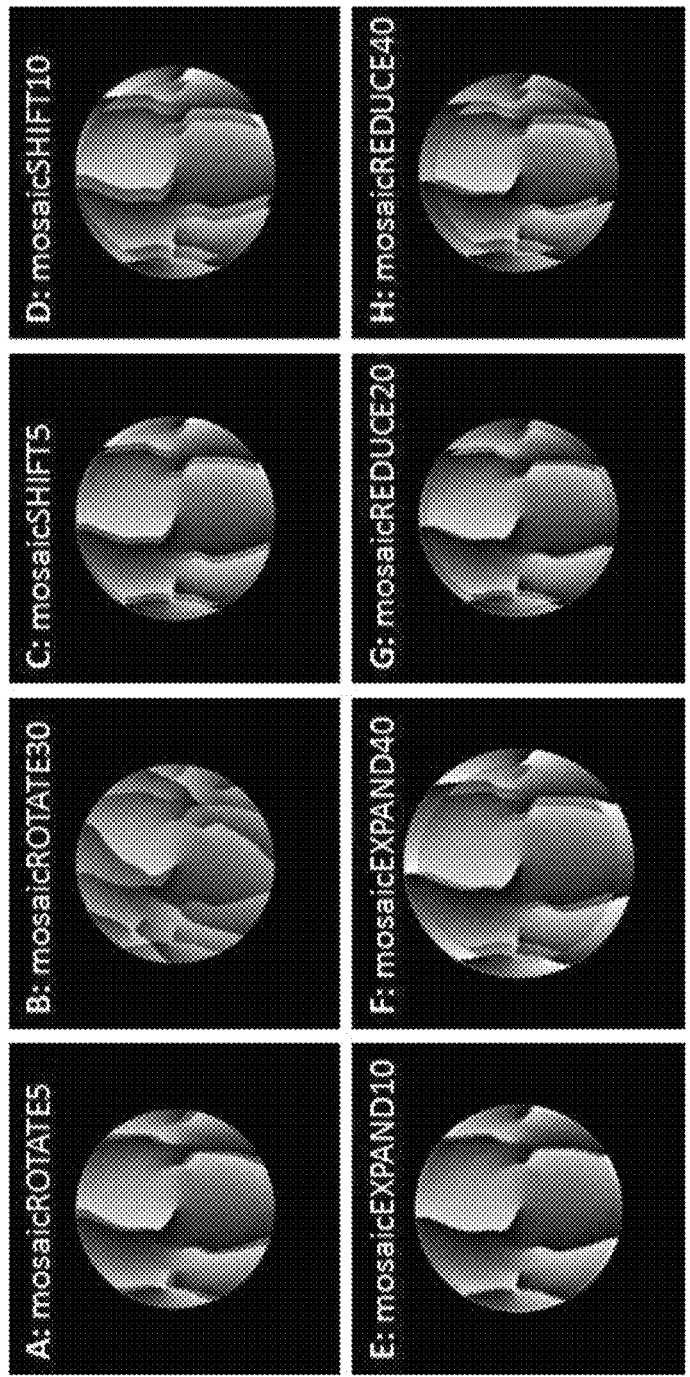
FIG. 26 Phase modulation pattern example 6

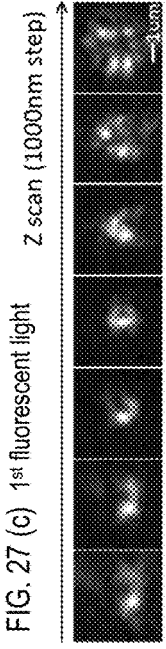

FIG. 27 (a) 1st fluorescent light   Z scan (1000nm step)

mosaicROTATE5

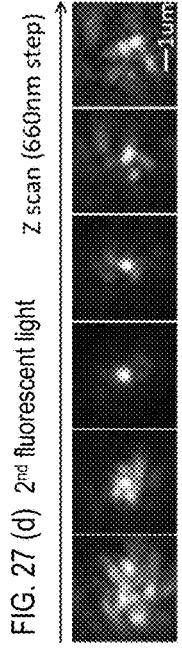

FIG. 27 (b) 2nd fluorescent light   Z scan (660nm step)

mosaicROTATE5

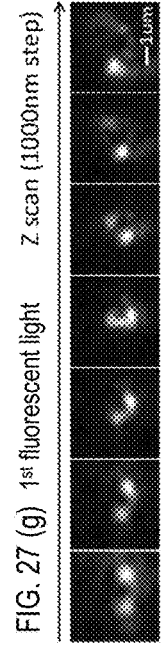

FIG. 27 (e) 1st fluorescent light   Z scan (1000nm step)

mosaicSHIFT5

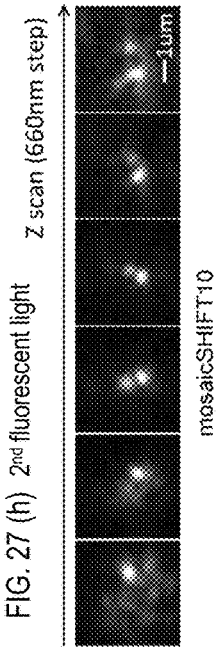

FIG. 27 (f) 2nd fluorescent light   Z scan (660nm step)

mosaicSHIFT5

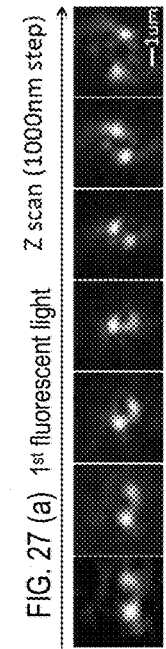

FIG. 27 (c) 1st fluorescent light   Z scan (1000nm step)

mosaicROTATE30

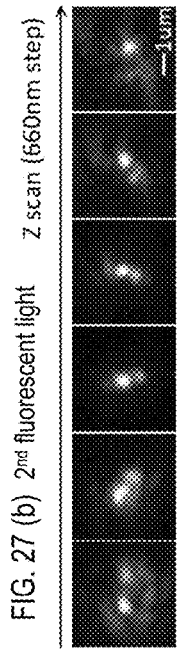

FIG. 27 (d) 2nd fluorescent light   Z scan (660nm step)

mosaicROTATE30

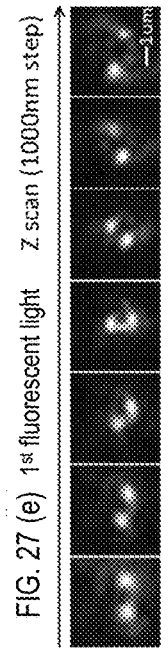

FIG. 27 (g) 1st fluorescent light   Z scan (1000nm step)

mosaicSHIFT10

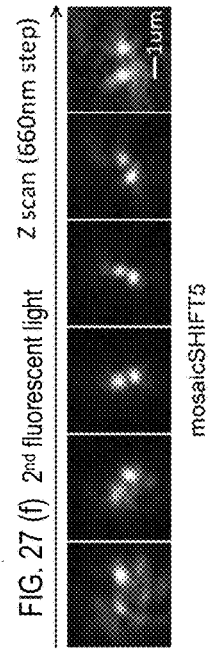

FIG. 27 (h) 2nd fluorescent light   Z scan (660nm step)

mosaicSHIFT10

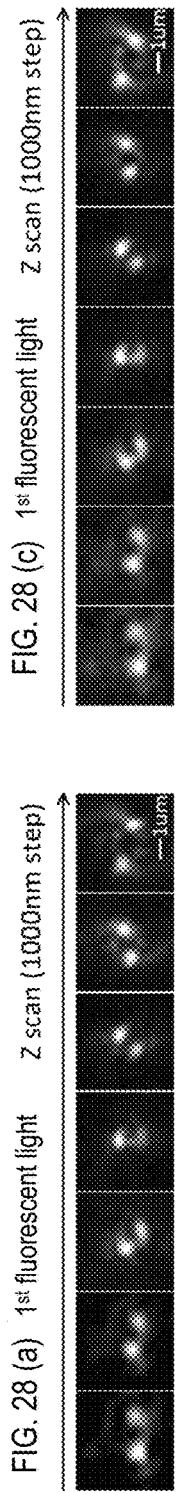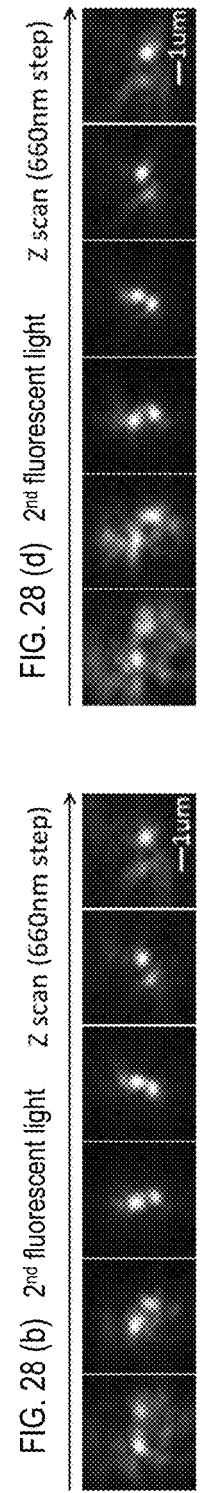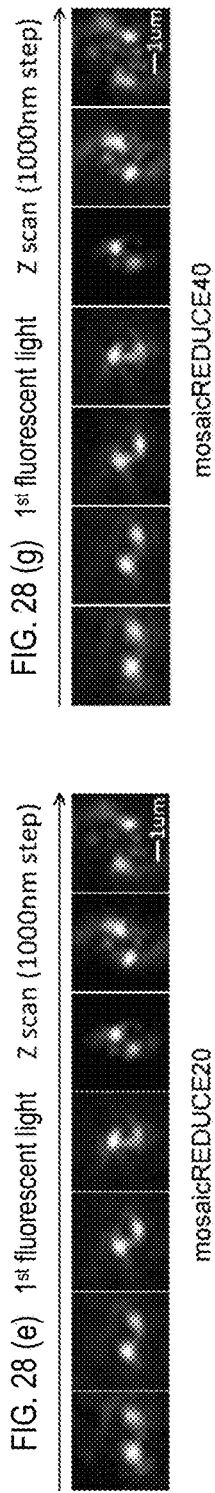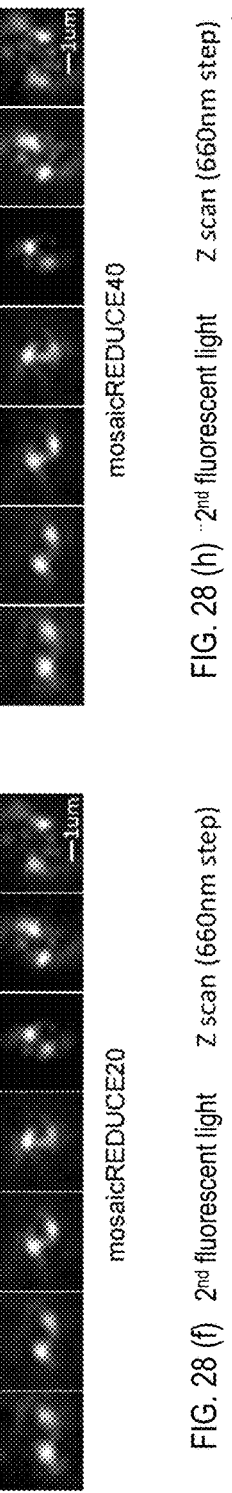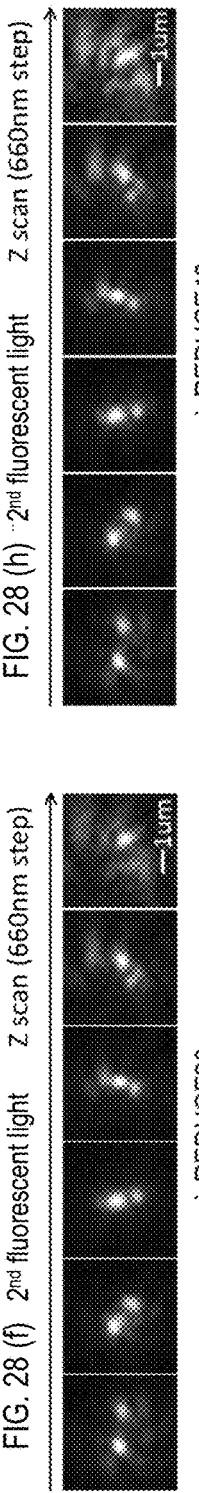

FIG. 28 (a) 1st fluorescent light  Z scan (1000nm step)  mosaicEXPAND10
FIG. 28 (b) 2nd fluorescent light  Z scan (660nm step)  mosaicEXPAND10
FIG. 28 (c) 1st fluorescent light  Z scan (1000nm step)  mosaicEXPAND40
FIG. 28 (d) 2nd fluorescent light  Z scan (660nm step)  mosaicEXPAND40
FIG. 28 (e) 1st fluorescent light  Z scan (1000nm step)  mosaicREDUCE20
FIG. 28 (f) 2nd fluorescent light  Z scan (660nm step)  mosaicREDUCE20
FIG. 28 (g) 1st fluorescent light  Z scan (1000nm step)  mosaicREDUCE40
FIG. 28 (h) 2nd fluorescent light  Z scan (660nm step)  mosaicREDUCE40

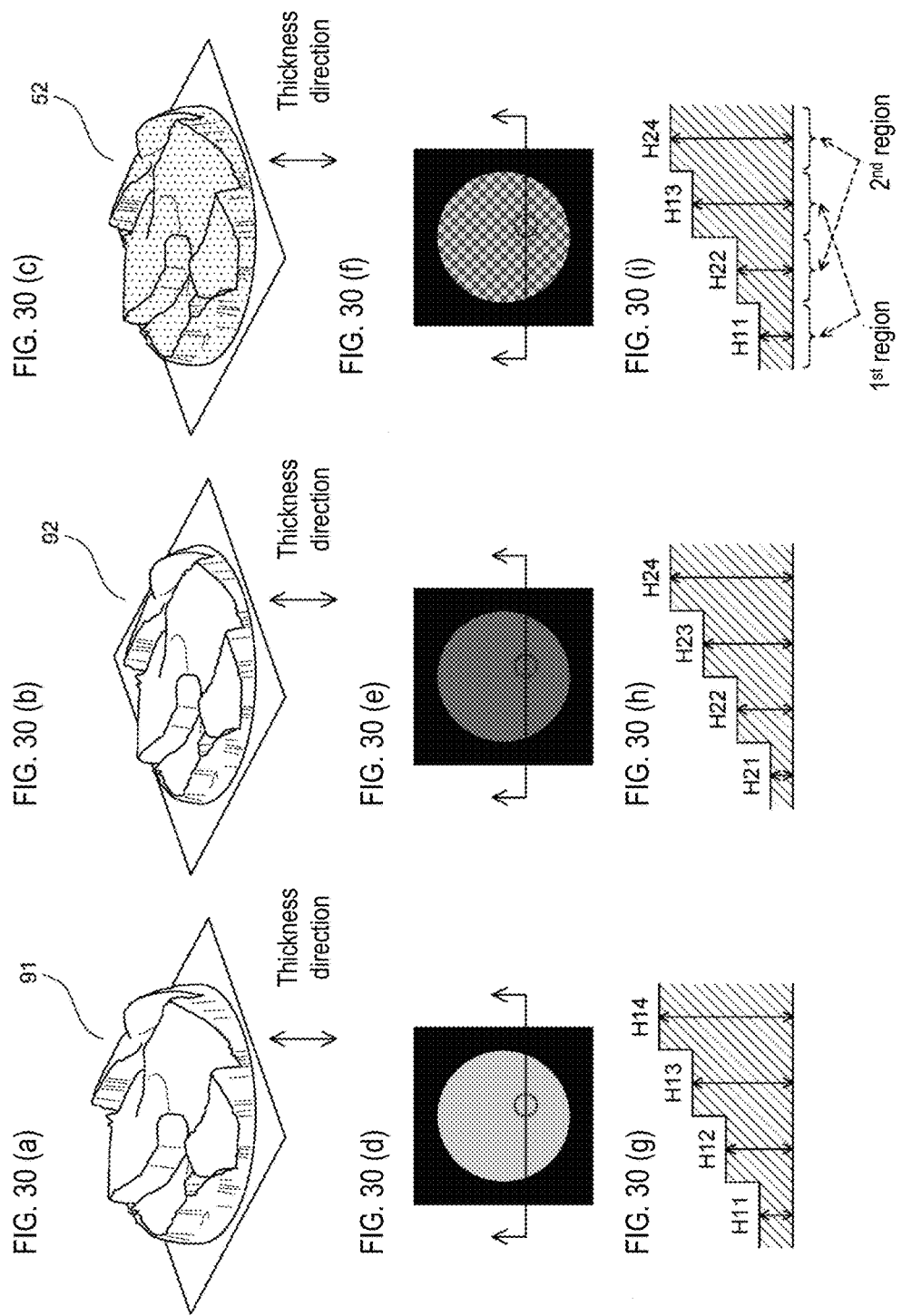

OPTICAL DEVICE, PHASE PLATE, AND IMAGE FORMING METHOD

CROSS REFERENCE TO RELATED APPLICATIONS

This application claim priority from prior Japanese Patent Application No. 2016-047682, filed on Mar. 10, 2016, entitled, "OPTICAL DEVICE, PHASE PLATE, AND IMAGE FORMING METHOD", the entire contents of which are incorporated herein by reference.

The present invention relates to an optical device, phase plate, and image forming method.

BACKGROUND

In optical devices such as optical microscopes, for example, various functions such as improvement of resolution and aberration correction are realized by using phase modulation of light. Patent reference 1 describes a phase modulation device that modulates phases of light fluxes of a plurality of different wavelengths within a predetermined broad spectrum width. The phase modulation device diffracts the light beam irradiated from the light source via a diffraction grating to different angles for each wavelength. The light beam diffracted for each wavelength enters the spatial phase modulation device through a condenser lens. The phase modulation device has a plurality of phase modulation areas respectively corresponding to the respective wavelengths, and the light flux of each wavelength is enters the phase modulation area corresponding to each wavelength by diffraction via the diffraction grating.

SUMMARY OF THE INVENTION

In the art of Japanese Patent Application Publication No. 2010-25922, the light flux must be diffracted by a diffraction grating, a prism, or the like in order to make the light flux enter the corresponding phase modulation region for each wavelength. A problem arises therefore in that the optical system becomes complex and the configuration for phase modulation becomes complicated. The phase modulation device of patent reference 1 also gives rise to the problem of phase modulation device becoming larger, since the phase modulation device has a plurality of phase modulation areas for each wavelength.

A first aspect invention relates to an optical device. The optical device of this embodiment includes a shared phase modulation mask that imparts a first phase modulation on light of a first wavelength and imparts a second phase modulation on light of a second wavelength, an irradiation optical system that causes the light of the first wavelength and the light of the second wavelength to be incident to the same incidence region on the phase modulation mask, and a light collecting optical system that collects the first phase-modulated light of the first wavelength and the second phase-modulated light of the second wavelength to form an image according to a point spread function.

A second aspect invention relates to an optical device. The optical device of this embodiment includes a shared phase modulation mask that imparts a phase modulation to light of a first wavelength and light of a second wavelength, an irradiation optical system that causes the light of the first wavelength and light of the second wavelength to be incident to the phase modulation mask, and a light collecting optical system that collects the light of the first wavelength and the light of the second wavelength that has been phase-modulated by the phase modulation mask to form an image according to a point spread function. The phase modulation mask is a phase plate. The phase plate has a thickness between the thickness of a phase plate for the light of the first wavelength and the thickness of a phase plate for the light of the second wavelength.

A third aspect invention relates to an optical device. The optical device of this embodiment includes a shared phase modulation mask that imparts a phase modulation to light of a first wavelength and light of a second wavelength, an irradiation optical system that causes the light of the first wavelength and light of the second wavelength to be incident to the phase modulation mask, and a light collecting optical system that collects the light of the first wavelength and the light of the second wavelength that has been phase-modulated by the phase modulation mask to form an image according to a point spread function. The phase modulation mask is a phase modulation device capable of setting a phase modulation pattern based on an input. The phase modulation device applies phase modulation to the light of the first wavelength and the light of the second wavelength by a phase modulation pattern set based on an input gradient between the gradient of the light of the first wavelength and the gradient of the light of the second wavelength.

A fourth aspect of the invention relates to a phase plate that causes light of a first wavelength and light of a second wavelength to be incident on the same incidence region. The phase plate of this embodiment includes a first region configured to apply a first phase modulation to light of the first wavelength, and a second region configured to apply a second phase modulation to light of the second wavelength in the incidence area, and the phase plate is configured to apply a first phase modulation on the light of the first wavelength and apply a second phase modulation on the light of the second wavelength.

A fifth aspect of the invention relates to a method for forming an image according to a point spread function from light of a first wavelength and light of a second wavelength. The image forming method of this embodiment causes light of a first wavelength and light of a second wavelength to be incident to the same incidence region in a shared phase modulation mask that imparts a first phase modulation on the light of the first wavelength and imparts a second phase modulation on the light of the second wavelength, uses the shared phase modulation mask to impart phase modulation to light of a first wavelength and light of the second wavelength and collects the first phase-modulated light of the first wavelength and the second phase-modulated light of the second wavelength to form an image according to a point spread function.

A sixth aspect of the invention relates to a method for forming an image according to a point spread function from light of a first wavelength and light of a second wavelength. The image forming method of this embodiment causes the light of the first wavelength and the light of the second wavelength to be incident on a shared phase plate that imparts phase modulation to the light of the first wavelength and the light of the second wavelength, the phase plate having a thickness between the thickness of a phase plate used for the light of the first wavelength and the thickness of a phase plate used for the light of the second wavelength, and collects the light of the first wavelength and the light of the second wavelength that has been modulated by the phase plate to form an image according to a point spread function.

A seventh aspect of the invention relates to a method for forming an image according to a point spread function from light of a first wavelength and light of a second wavelength. The image forming method of this embodiment causing the light of the first wavelength and the light of the second wavelength to be incident to a shared phase modulation device that imparts phase modulation to the light of the first wavelength and the light of the second wavelength by a phase modulation pattern set based by an input of a gradation between the gradation for the light of the first wavelength and the gradation for the light of the second wavelength, collects the light of the first wavelength and the light of the second wavelength that has been phase modulated by the phase modulation device to form an image according to a point spread function.

BRIEF DESCRIPTION OF THE DRAWINGS

FIG. 2 (a) is a schematic view showing two bright spot images rotated on the imaging plane according to the position of the emission point of fluorescence in the Z axis direction of the embodiment; FIG. 2 (b) shows the DH-PSF of the embodiment;

FIG. 3 (b) is a schematic view showing the inactive state of all first fluorescence dye of the embodiment; FIGS. 3 (c) and 3 (d) are schematic views showing the active state of part of the first fluorescence dye of the embodiment; FIG. 3 (e) is a schematic view showing the active state of all second fluorescence dye of the embodiment; FIG. 3 (f) is a schematic view showing the inactive state of all second fluorescence dye of the embodiment;

FIGS. 3 (g) and 3 (h) are schematic views showing the active state of part of the second fluorescence dye of the embodiment;

FIG. 4 (a) through 4 (e) are schematic views showing the sequence of obtaining a first 3-dimensional super-resolution image of the embodiment; FIG. 4 (f) is a schematic view showing the sequence of obtaining the number of a first substance of the embodiment;

FIG. 5 (b) is a schematic view showing the first and second 3-dimensional super-resolution images obtained from a plurality of common 2-dimensional images in a modification of the embodiment;

FIG. 6 (a) is a schematic view showing the structure of the optical device provided with a phase modulation mask of the embodiment; FIG. 6 (b) is a schematic view showing the structure of the phase modulation device of the embodiment;

FIGS. 7 (a) and 7 (b) show the first phase modulation pattern and second phase modulation pattern set in the phase modulation device of the embodiment;

FIGS. 8 (a) and 8 (b) show the imaging state and graph when the first fluorescent light is observed using the first phase modulation pattern of the embodiment; FIGS. 8 (c) and 8 (d) show the imaging state and graph when the second fluorescent light is observed using the first phase modulation pattern of the embodiment; FIGS. 8 (e) and 8 (f) show the imaging state and graph when the first fluorescent light is observed using the second phase modulation pattern of the embodiment; FIGS. 8 (g) and 8 (h) show the imaging state and graph when the second fluorescent light is observed using the second phase modulation pattern of the embodiment;

FIGS. 12 (a) and 12 (b) show the imaging state and graph when the first fluorescent light is observed using the first phase modulation pattern of example 1; FIGS. 12 (c) and 12 (d) show the imaging state and graph when the second fluorescent light is observed using the first phase modulation pattern of example 1;

FIG. 13 (a) through 13 (c) illustrate details of the integration of the first phase modulation pattern and second phase modulation pattern according to the phase modulation pattern of example 1; FIG. 13 (a) through 13 (c) schematically show one pixel position on a liquid crystal panel in the first phase modulation pattern, second phase modulation pattern, and the phase modulation pattern of example 1, respectively;

FIG. 14 (a) is a schematic diagram showing the arrangement of regions in the phase modulation pattern of example 2; FIG. 14 (b) through 14 (d) schematic diagrams showing the structure of the phase modulation pattern of example 2;

FIGS. 15 (a) and 15 (b) show the imaging state and graph when the first fluorescent light is observed using the phase modulation pattern of example 2; FIGS. 15 (c) and 15 (d) show the imaging state and graph when the second fluorescent light is observed using the phase modulation pattern of example 2; FIGS. 15 (e) and 15 (f) show the imaging state and graph when the first fluorescent light and second fluorescent light is observed using the phase modulation pattern of example 2;

FIGS. 16 (a) and 16 (b) show the result of observing the first fluorescent light and the second fluorescent light with a wide field of view using the phase modulation pattern of example 2;

FIG. 17 (a) is a schematic diagram showing the arrangement of regions in the phase modulation pattern of example 3; FIG. 17 (b) through 17 (d) schematic diagrams showing the structure of the phase modulation pattern of example 3;

FIGS. 18 (a) and 18 (b) show the imaging state and graph when the first fluorescent light is observed using the phase modulation pattern of example 3; FIGS. 18 (c) and 18 (d) show the imaging state and graph when the second fluorescent light is observed using the phase modulation pattern of example 3; FIGS. 18 (e) and 18 (f) show the imaging state and graph when the first fluorescent light and second fluorescent light is observed using the phase modulation pattern of example 3;

FIGS. 19 (a) and 19 (b) respectively show the result of observing the first fluorescent light and the second fluorescent light with a wide field of view using the phase modulation pattern of example 3;

FIG. 20 (a) is a schematic diagram showing the arrangement of regions in the phase modulation pattern of example 3; FIG. 20 (b) through 20 (d) are schematic diagrams showing the structure of the phase modulation pattern of example 4;

FIGS. 21 (a) and 21 (b) show the imaging state and graph when the first fluorescent light is observed using the phase modulation pattern of example 4; FIGS. 21 (c) and 21 (d) show the imaging state and graph when the second fluorescent light is observed using the phase modulation pattern of example 4; FIGS. 21 (e) and 21 (f) show the imaging state and graph when the first fluorescent light and second fluorescent light is observed using the phase modulation pattern of example 4;

FIGS. 22 (a) and 22 (b) show the result of observing the first fluorescent light and the second fluorescent light with a wide field of view using the phase modulation pattern of example 4;

FIG. 23 (a) is a schematic diagram showing the arrangement of regions in the phase modulation pattern of example 5; FIG. 23 (b) through 23 (e) are schematic diagrams showing the structure of the phase modulation pattern of example 5;

FIGS. 24 (a) and 24 (b) show the imaging state and graph when the first fluorescent light is observed using the phase modulation pattern of example 5; FIGS. 24 (c) and 24 (d) show the imaging state and graph when the second fluorescent light is observed using the phase modulation pattern of example 5; FIGS. 24 (e) and 24 (g) show the imaging state and graph when the first fluorescent light is observed using the phase modulation pattern of example 5; FIGS. 24 (f) and 24 (h) show the imaging state and graph when the second fluorescent light is observed using the phase modulation pattern of example 5;

FIGS. 25 (a) and 25(b) show the result of observing the first fluorescent light and the second fluorescent light with a wide field of view using the phase modulation pattern of example 5;

FIG. 26 shows the structure of a phase modulation pattern of example 6;

FIGS. 27 (a), 27 (c), 27 (e), and 27 (g) show the imaging state when the first fluorescent light is observed using the phase modulation pattern of example 6; FIGS. 27 (b), 27 (d), 27 (f), and 27 (h) show the imaging state when the second fluorescent light is observed using the phase modulation pattern of example 6;

FIGS. 28 (a), 28 (c), 28 (e), and 28 (g) show the imaging state when the first fluorescent light is observed using the phase modulation pattern of example 6; FIGS. 28 (b), 28 (d), 28 (f), and 28 (h) show the imaging state when the second fluorescent light is observed using the phase modulation pattern of example 6;

FIG. 29 (b) is a schematic view showing the phase plate manufactured so as to correspond to the second phase modulation pattern of the embodiment; FIG. 29 (c) a schematic view showing a phase plate integrated as in the phase modulation pattern of example 1; FIG. 29 (d) through 29 (f) are schematic views showing cross sections when the phase plate according to the embodiment is sectioned along a plane parallel to the thickness direction;

FIG. 30 (a) is a schematic view showing the phase plate manufactured so as to correspond to the first phase modulation pattern of the embodiment; FIG. 30 (b) is a schematic view showing the phase plate manufactured so as to correspond to the second phase modulation pattern of the embodiment; FIG. 30 (c) a schematic view showing a phase plate integrated as in the phase modulation pattern of example 2; FIG. 30 (d) through 30 (f) schematically shows regions when viewing in the thickness direction of the phase plate of the embodiment; and FIG. 30 (g) through 30 (i) are schematic views showing cross sections when the phase plate according to the embodiment is sectioned along a plane parallel to the thickness direction.

DESCRIPTION OF THE EMBODIMENTS OF THE INVENTION

The following embodiments apply the invention to optical devices for observing two types of fluorescent light with different center wavelengths. The optical device of the embodiment is a fluorescence microscope that irradiates light on a sample and captures the fluorescent light given off from the sample via an imaging part. The optical device to which the invention can be applied is not limited to the following embodiments, and may be a microscope other than a fluorescence microscope, that is, an imaging device such as a camera, a telescope, an endoscope, a planetarium or the like. The optical device to which the invention can be applied also is not limited to a device for imaging and observing fluorescent light, and may be a device for imaging and observing light other than fluorescent light.

Figure 1:
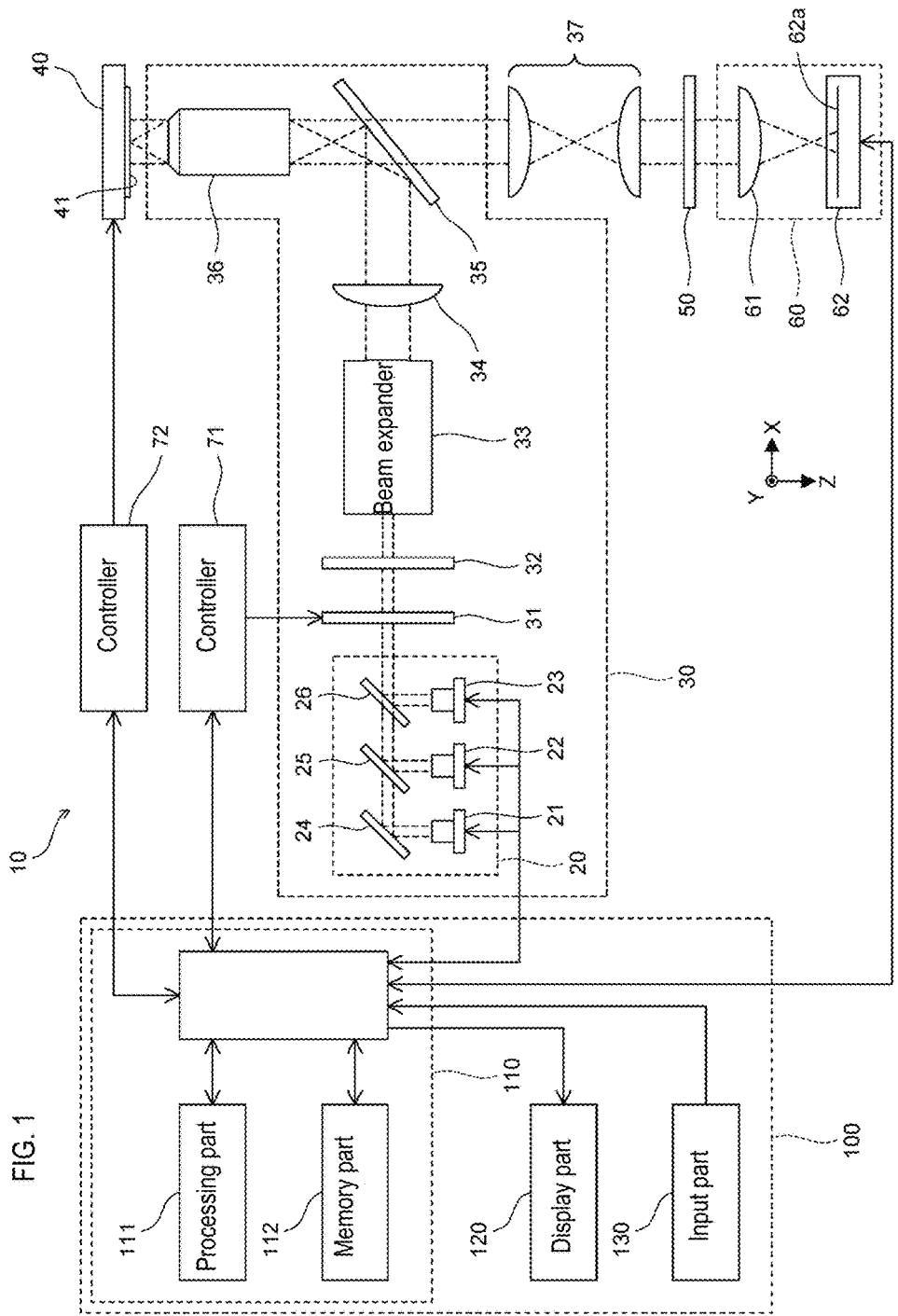
FIG. 1 is a schematic view showing the structure of the optical device provided with a phase modulation mask of the embodiment.

As shown in FIG. 1, the optical device 10 is provided with an irradiating optical system 30, beam expander 37, stage 40, phase modulation mask 50, light collecting optical system 60, controllers 71 and 72, and information processing device 100. Mutually orthogonal XYZ axes are shown in FIG. 1.

A slide glass 41 on which a sample is placed is installed on the stage 40. The sample of the embodiment is a biological sample containing test cells. The test cells, for example, are collected from diseased tissue. The nucleus of the test cell contains a first substance and a second substance. The first substance and the second substance to be imaged are, for example, biological substances such as genes, proteins or peptides that may be disease markers. The first substance of the embodiment is the HER2 gene, and the second substance of the embodiment is CEP17 which is a centromere region of chromosome 17.

Fluorescent substances are bound to the first substance and the second substance, respectively, when preparing the sample. In the embodiment, the fluorescent substance bound to the first substance is a first fluorescent dye, and the fluorescent substance bound to the second substance is a second fluorescent dye. The nucleus of the test cells also are specifically stained by a third fluorescent dye when preparing the sample.

The first fluorescent dye can be switched between an active state in which a first fluorescent light having a center wavelength of a first wavelength is given off when irradiated with light from a light source 21 (described later), and an inactive state in which the first fluorescent light is not given off even when irradiated by light from the light source 21. The first fluorescent dye is inactivated when irradiated with light from the light source 21, and is activated when light from a light source 23 to be described later. The second fluorescent dye can be switched between an active state in which a second fluorescent light having a center wavelength of a second wavelength is given off when irradiated with light from a light source 22 (described later), and an inactive state in which the second fluorescent light is not given off even when irradiated by light from the light source 22. The second fluorescent dye is inactivated when irradiated with light from the light source 22, and is activated when light from the light source 23. The third fluorescent dye gives off a third fluorescent light having a center wavelength of a third wavelength when irradiated by light from the light source 23.

The substance to be imaged is not limited to the fluorescent dye that binds to the substance as described above, and may be a substance that produces autofluorescence. The sample placed on the slide glass 41 is not limited to a biological sample. The substance to be imaged is not limited to a substance contained in a biological sample, and may be a substance not derived from the biological sample. For example, the substance to be imaged may be fluorescent beads or fluorescent substances such as fluorescent particles and the like.

The irradiation optical system 30 includes a light source section 20, a shutter 31, a quarter-wave plate 32, a beam expander 33, a condenser lens 34, a dichroic mirror 35, and an objective lens 36. The irradiation optical system 30 irradiates the sample with light to generate first through third fluorescent lights from the fluorescently labeled first through third substances contained in the sample, respectively, and causes the first fluorescent light and the second fluorescent light to be incident on the same incident region in the phase modulation mask 50.

The light source section 20 includes light sources 21 through 23, mirror 24, and dichroic mirrors 25 and 26.

The light sources 21 through 23 respectively emit light of different wavelengths. Specifically, the wavelengths of the light emitted from the light sources 21, 22 and 23 are 640 nm, 488 nm, and 405 nm, respectively. A laser light source is preferably used, but a mercury lamp, a xenon lamp, an LED, or the like may be used as the light sources 21 through 23. As described above, the light emitted from the light source 21 excites the first fluorescent dye contained in the test cell to generate the first fluorescent light, and inactivates the first fluorescent dye. The light emitted from the light source 22 excites the second fluorescent dye contained in the test cell to generate the second fluorescent light, and inactivates the second fluorescent dye. The light emitted from the light source 23 excites the third fluorescent dye contained in the test cell to generate the third fluorescent light, and inactivates the third fluorescent dye. Note that, in the embodiment, the first wavelength that is the center wavelength of the first fluorescent light is 690 nm, and the second wavelength that is the center wavelength of the second fluorescent light is 530 nm.

The mirror 24 reflects the light from the light source 21. The dichroic mirror 25 transmits the light from the light source 21 and reflects the light from the light source 22. The dichroic mirror 26 transmits the light from the light sources 21 and 22, and reflects the light from the light source 23. The optical axes of the light from the light sources 21 through 23 are mutually matched by the mirror 24 and dichroic mirrors 25 and 26. Note that one light source may emit light having wavelengths of 640 nm, 488 nm, and 405 nm instead of the light sources 21 through 23.

The shutter 31 is driven by the controller 71 and switches between a state of allowing light emitted from the light source section 20 to pass through and a state of blocking light emitted from the light source section 20. In this way the irradiation time of light on the test cell is adjusted. The quarter-wave plate 32 converts the linearly polarized light emitted from the light source section 20 into circularly polarized light. The fluorescent dye reacts to light of a predetermined polarization direction. Therefore, the polarization direction of the excitation light is easily matched to the polarization direction in which the fluorescent dye reacts by converting the excitation light emitted from the light source section 20 into circularly polarized light. In this way it is possible to excite fluorescence efficiently in the fluorescent dye contained in the test cell. The beam expander 33 expands the irradiation area of the light on the slide glass 41. The condenser lens 34 condenses the light so that parallel light is emitted from the objective lens 36 to the slide glass 41.

Dichroic mirror 35 reflects the light emitted from the light source section 20, and transmits fluorescent light given off from the test cell. The objective lens 36 guides the light reflected by the dichroic mirror 35 to the slide glass 41. The stage 40 is driven by the controller 72 and moves on the horizontal plane within the X-Y plane. The fluorescent light given off from the test cells passes through the objective lens 36, passes through the dichroic mirror 35, and is rendered to parallel light by the beam expander 37.

The phase modulation mask 50 provides phase modulation for the first fluorescent light and the second fluorescent light. The phase modulation mask 50 is disposed on the Fourier plane of the optical system formed by the objective lens 36, the dichroic mirror 35, the beam expander 37, and the condenser lens 61, and has the effect of modulating the phase of the light incident on the same incident region of the phase modulation mask 50.

Note that when the phase difference is "θ", and when the phase difference is "θ+n×2π" (where n=±0, 1, 2, 3 . . . ), the phase difference given to the fluorescent light is substantially the same. Therefore, the phase difference given to the first fluorescent light and the phase difference given to the second fluorescent light by the phase modulation mask 50 is not limited to a single value, and also may be a value obtained by adding n×2π to the single value.

The phase modulation mask 50 is arranged as shown in FIG. 1 when modulating the phase of the light passing through the phase modulation mask 50. The phase modulation mask 50 that modulates the phase of the transmitted light is configured by, for example, a phase plate made of a transparent member such as an acrylic resin, a phase modulation device with a liquid crystal panel or the like.

The phase modulation mask 50 is arranged as shown in FIG. 6 (a) when modulating the phase of the light reflected by the phase modulation mask 50. The phase modulation mask 50 that modulates the phase of the reflected light is configured by, for example, a phase modulation device with a liquid crystal panel, a deformable mirror, a reflecting member configured similarly to a deformable mirror and the like. Note that when the phase modulation mask 50 is configured by a phase modulation device having a liquid crystal panel, a polarizing plate 38 and a mirror 39 are arranged instead of the beam expander 37, as shown in FIG. 6 (a), and the mask 50 is arranged at the position of the phase modulation device 51. When the phase modulation mask 50 is configured by a deformable mirror, a reflecting member constructed similarly to a deformable mirror or the like, the polarizing plate 38 is omitted from the configuration shown in FIG. 6 (a), and the phase modulation mask 50 is arranged at the position of the phase modulation device 51.

A configuration example of the phase modulation mask 50 that modulates the phase of the transmitted light will be described later with reference to FIGS. 29 (a) to 30 (i). A configuration example of the phase modulation mask 50 that modulates the phase of the reflected light will be described later with reference to FIGS. 6 (a) to 28 (h).

The phase modulation mask 50 forms an image according to the point spread function of the first fluorescent light given off from the first fluorescent dye, and forms an image according to the point spread function of the second fluorescent light given off from the second fluorescent dye. In the phase modulation mask 50 of the embodiment, the first fluorescent light given off from one first fluorescent dye is imaged at two focal points on the imaging surface 62a of the imaging part 62, and the second fluorescent light given off from one second fluorescent dye is imaged at two focal points on the imaging surface 62a of the imaging unit 62.

Such a point spread function is called DH-PSF (Double-Helix Point Spread Function). The phase modulation mask 50 modulates the phases of the first fluorescent light and the second fluorescent light entering the Fourier plane, and forms an image corresponding to the DH-PSF on the imaging surface 62a for both the first fluorescent light and the second fluorescent light.

Note that the phase modulation mask 50 is not configured to form an image according to the DH-PSF on the imaging surface 62a for the third fluorescent light, unlike the case of the first fluorescent light and the second fluorescent like. The reason for this is that, as will be described later, the third fluorescent light is used only for identifying the region of the nucleus. Although the phase of the third fluorescent light transmitted through the phase modulation mask 50 is modulated somewhat by the phase modulation mask 50, it is possible to sufficiently identify the region of the nucleus if the third fluorescent light is imaged by the imaging part 62.

The flight collecting optical system 60 condenses the phase-modulated first fluorescent light and the second fluorescent light to form an image corresponding to the DH-PSF. The light collecting optical system 60 includes a collective lens 61 and imaging part 62. The collective lens 61 collects the fluorescent light that passes through the phase modulation mask 50, and guides the fluorescent light to the imaging surface 62a of the imaging part 62. The imaging part 62 captures an image of the fluorescent light irradiated on the imaging surface 62a, and generates a two-dimensional image. The imaging part 62 is configured by, for example, a CCD or the like.

Here, as described above, the first fluorescent light given off from one first fluorescent dye and the second fluorescent light given off from one second fluorescent dye are formed at to focal points on the imaging surface 62a via the function of the phase modulation mask 50. That is, an image corresponding to the DH-PSF of the first fluorescent light and the second fluorescent light is formed on the imaging surface 62a. At this time, due to the action of the phase modulation mask 50, the bright spot images respectively corresponding to the two focal points are shifted in the Z axis direction, that is, rotated and formed on the imaging surface 62a according to position of the fluorescent light emitting point in the depth direction of the slide glass 41, as shown in FIG. 2 (a), through the action of the phase modulation mask 50. That is, the angle formed by the line connecting the two bright spot images and the reference line changes on the imaging surface 62a according to the position of the emission point of the fluorescent light in the Z axis direction.

That is, the phase modulation mask 50 is configured to modulate the phase of the first fluorescent light so as to form a DH-PSF in which two bright spot images of the first fluorescent light rotate on the imaging surface 62a according to the distance between the objective lens 36 and the first fluorescent dye in the sample. Similarly, the phase modulation mask 50 is configured to modulate the phase of the second fluorescent light so as to form a DH-PSF in which two bright spot images of the second fluorescent light rotate on the imaging surface 62a according to the distance between the objective lens 36 and the second fluorescent dye in the sample.

For example, the fluorescent light given off from the fluorescent dyes at two different positions in the Z-axis direction on the slide glass 41 is divided into two by the phase modulation mask 50 and irradiated onto the imaging surface 62a. At this time, the straight line connecting the two bright spot images on the imaging surface 62a forms an angle of $+\theta 1$ with the reference line for one of the fluorescent dyes, for example, and forms an angle of $+\theta 2$ with the reference line relative to the other fluorescent dye, as shown in FIG. 2 (a). Therefore, if a straight line connecting the two bright spot images acquires an angle formed with respect to the reference line, the position of the fluorescent dye in the Z axis direction can be acquired. In the embodiment, regarding the first fluorescent light and the second fluorescent light, the position in the Z-axis direction is acquired as described above based on the two-dimensional image captured by the imaging part 62.

Note that DH-PSF can be represented by the equation shown in FIG. 2 (b). In the equation of FIG. 2 (b), 'bright spot 1' and 'bright spot 2' represents the two bright spot images formed on the imaging surface 62a, as shown in FIG. 2 (a). 'Coordinates on the imaging surface' represent the coordinates on the imaging surface 62a of the fluorescent dyes that are the source of the two bright spot images.

As described above, both the first fluorescent light and the second fluorescent light are incident on the same incident area of the phase modulation mask 50, and the phase modulation mask 50 respectively modulates the phase of the first fluorescent light and the second fluorescent light which have mutually different wavelengths. In this way, it is not necessary to guide the first fluorescent light to a region for modulating the phase of the first fluorescent light, or to guide the second fluorescent light to a region for modulating the phase of the second fluorescent light. Therefore, since there is no need to separately provide the phase modulation area of the first fluorescent light and the phase modulation area of the second fluorescent light, there is no need for a diffraction grating to diffract the flux or a prism to divide the flux in order to guide the first fluorescent light and the second fluorescent light to separate phase modulation areas. Therefore, according to the phase modulation mask 50, the phase can be modulated with respect to both the first fluorescent light and the second fluorescent light with a simple configuration, and an image corresponding to the DH-PSF of the first fluorescent light and the second fluorescent light can be formed.

When the first fluorescent light and the second fluorescent light are split into different optical paths, there also is a possibility that an image corresponding to the desired DH-PSF can not be formed due to misalignment during the assembly of the optical elements of the respective optical paths. However, according to the phase modulation mask 50, it is possible to suppress the influence caused by misalignment during the assembly of the optical elements the like since an optical element for branching the optical path becomes unnecessary. Therefore, it is possible to generate a highly accurate two-dimensional image. Such improvement of the accuracy of the two-dimensional image is particularly desirable in the optical device 10 of the embodiment for generating a three-dimensional super-resolution image which will be described later.

Returning to FIG. 1, the information processing device 100 is a personal computer that includes a body 110, display part 120, and input part 130. The body 110 includes a processing part 111, memory part 112, and interface 113.

The processing part 111, for example, may be configured by a CPU. The memory part 112, for example, may be configured by a ROM, RAM, hard disk or the like. The processing part 111 controls the light sources 21 through 23 of the light source section 20, imaging part 62, and controller 71 and 72 through the interface 113 based on a program stored in the memory part 112.

The processing part 111 acquires the position in the Z-axis direction of the light emission point of the first fluorescent light as described above based on the two-dimensional image of the first fluorescent light to generate a three-dimensional super-resolution image of the first fluorescent light. Similarly, the processing part 111 acquires the position in the Z-axis direction of the light emission point of the second fluorescent light as described above based on the two-dimensional image of the second fluorescent light to generate a three-dimensional super-resolution image of the second fluorescent light. Hereinafter, the two-dimensional image of the first fluorescent light is referred to as a "first two-dimensional image", the two-dimensional image of the second fluorescent light is referred to as a "second two-dimensional image", and the two-dimensional image of the third fluorescent light is referred to as the "third two-dimensional image". The three-dimensional super-resolution image of the first fluorescent light is referred to as a "first three-dimensional super-resolution image" and the three-dimensional super-resolution image of the second fluorescent light is referred to as a "second three-dimensional super-resolution image".

The display part 120 is a display for showing the processing results and the like of the processing part 111. The input part 130 is a mouse and keyboard for receiving input instructions from a user.

Next, the generation procedure of the first and second three-dimensional super-resolution images will be described.

First, the procedure for acquiring the first two-dimensional image will be described referring to FIGS. 3 (a) to 3 (d).

Figure 3:
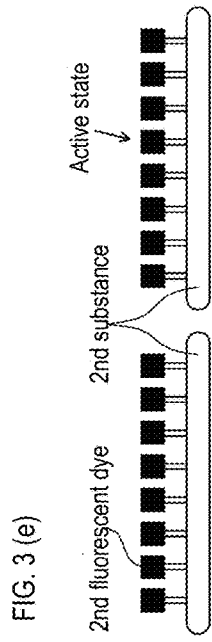
FIG. 3 (a) is a schematic view showing the active state of all first fluorescence dye of the embodiment.
Figure 3:
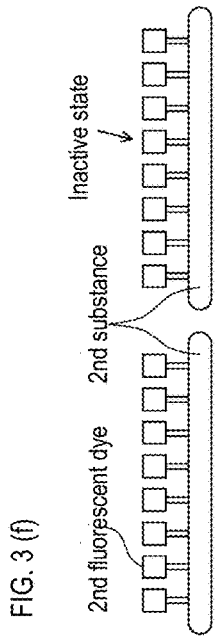
Figure 3:
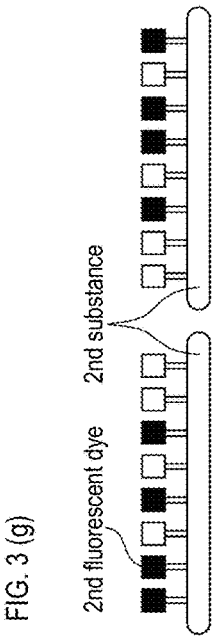
Figure 3:
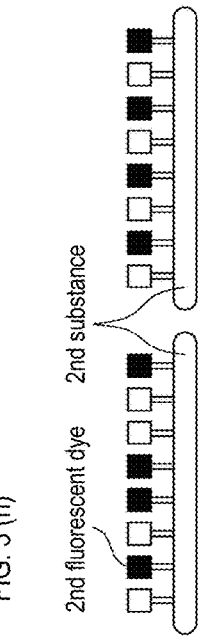
Figure 3:
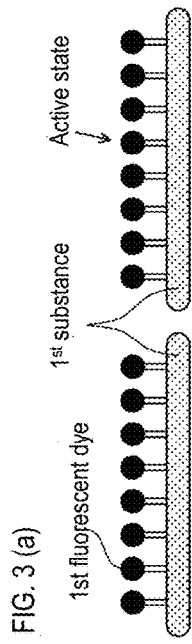
Figure 3:
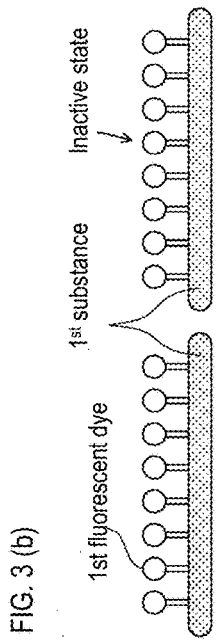
Figure 3:
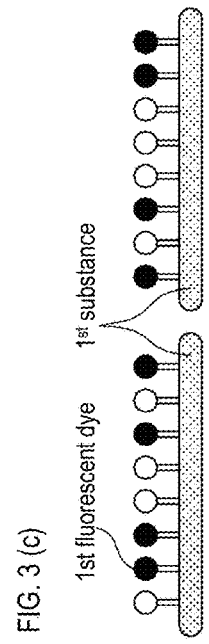
Figure 3:
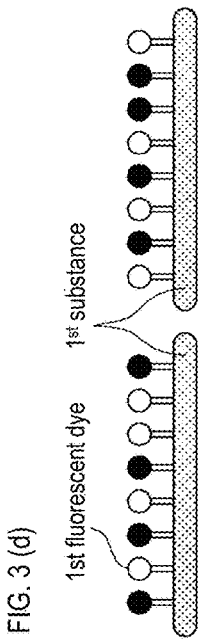

As shown in FIG. 3 (a), In the preparation of the sample, the first fluorescent dye is bound to the first substance via an intermediate substance that specifically binds to the first substance. Since the first substance is a gene, a nucleic acid probe can be used as an intermediate substance. A plurality of first fluorescent dyes is bound to one first substance. FIG. 3 (a) schematically shows two first substances to which the first fluorescent dye is bound, respectively. In the initial state, all the first fluorescent dyes are active. When the test cell is irradiated with light from the light source 21 for a predetermined time in the state shown in FIG. 3 (a), all the first fluorescent dyes become inactive as shown in FIG. 3 (b).

When the test cell is irradiated with light from the light source 23 for a predetermined time in the state shown in FIG. 3 (a), some of the first fluorescent dyes become active as shown in FIG. 3 (c). The ratio of the first fluorescent dye to be activated changes by adjusting the irradiation time of light from the light source 23. When the test cell is irradiated with the light from the light source 21 again for a predetermined time in the state shown in FIG. 3 (c), the first fluorescent light is given off from the activated first fluorescent dye, then all the first fluorescent dyes enter the inactive state as shown in FIG. 3 (b).

When the test cell is irradiated with light from the light source 23 again for a predetermined time, some of the first fluorescent dyes become active as shown in FIG. 3 (d), for example. When the test cell is irradiated with the light from the light source 21 again for a predetermined time in the state shown in FIG. 3 (d), the first fluorescent light is given off from the activated first fluorescent dye, then all the first fluorescent dyes enter the inactive state as shown in FIG. 3 (b). As shown in FIGS. 3 (c) and 3 (d), the distribution of the first fluorescent dye activated in each activation process is different each time.

The processing part 111 drives the light sources 21 and 23 to repeatedly activate and deactivate the first fluorescent dye as described above. The imaging part 62 images the distribution of the first fluorescent dye which is different each time. In this way, the processing part 111 acquires a plurality of first two-dimensional images, for example, 3000 first two-dimensional images.

The procedure for acquiring the second two-dimensional image will be described below with reference to FIGS. 3 (e) to 3 (h). The acquisition of the second two-dimensional image is performed in substantially the same manner as acquisition of the first two-dimensional image.

When the test cell is irradiated with light from the light source 22 for a predetermined time in the initial state shown in FIG. 3 (e), all the second fluorescent dyes become inactive as shown in FIG. 3 (f). When the test cell is irradiated with light from the light source 23 for a predetermined time in the state shown in FIG. 3 (f), some of the second fluorescent dyes become active as shown in FIG. 3 (g). When the test cell is irradiated with the light from the light source 22 again for a predetermined time in the state shown in FIG. 3 (g), the second fluorescent light is given off from the activated second fluorescent dye, then all the second fluorescent dyes become inactive state as shown in FIG. 3 (f). When the test cell is irradiated with light from the light source 23 again for a predetermined time, some of the second fluorescent dyes become active as shown in FIG. 3 (h), for example.

The processing part 111 drives the light sources 22 and 23 to repeatedly activate and deactivate the second fluorescent dye as described above. The imaging part 62 images the distribution of the second fluorescent dye which is different each time. In this way, the processing part 111 acquires a plurality of second two-dimensional images, for example, 3000 first two-dimensional images.

The procedure for generating the first three-dimensional super-resolution image will be described below with reference to FIGS. 4 (a) to 4 (e). Note that since the procedure of generating the second three-dimensional super-resolution image is the same as that of the first three-dimensional super-resolved image, only the procedure of generating the first three-dimensional super-resolved image will be described below.

As shown in FIG. 4 (a), a plurality of first two-dimensional images is acquired as described above. On the first two-dimensional image shown in FIG. 4 (a), the captured first fluorescent light is indicated by black circles. As shown in FIG. 4 (b), the processing part 111 extracts the first fluorescent bright spot 81 by Gaussian fitting in each of the first two-dimensional images. Then, the processing part 111 acquires the coordinates and brightness in the X-Y plane with respect to the extracted bright spot 81.

Subsequently, the processing part 111 refers to two bright spots 81 having similar brightness at a distance within a predetermined range. The processing part 111 causes the referenced to two bright spots 81 to be fitted with the templates of the two bright spots stored in advance in the storage unit 112. The processing part 111 pairs the two bright spots 81 that can be fitted with a certain accuracy or higher, assuming that the first fluorescent light given off from one first fluorescent dye is divided by the phase modulation mask 50.

Then, as shown in FIG. 4 (c), the processing part 111 obtains a point 82 on the X-Y plane of the first fluorescent dye which is the source of the two bright spots 81 based on the pair of two bright spots 81. Subsequently, as shown in FIG. 4 (d), the processing part 111 acquires an angle θ between the reference line and a straight line connecting the pair of two bright spots 81. The processing part 111 calculates the coordinates of the first fluorescent dye in the Z-axis direction based on the acquired angle θ. In this manner, as shown in FIG. 4 (*e*), the processing part 111 acquires the three-dimensional coordinates of the plurality of first fluorescent dyes based on the coordinates in the X-Y plane and the coordinates in the Z axis direction. Then, as shown in FIG. 4 (*e*), the processing part 111 generates a first three-dimensional super-resolution image by superimposing the plurality of three-dimensional coordinates acquired in each of the first two-dimensional images.

In this manner, when the first and second three-dimensional super-resolution images are acquired, the light emission points of the first fluorescent light and the light emission points of the second fluorescent light can be accurately grasped compared to when the first and second two-dimensional images are used. As a result, a physician or the like can comprehend the distribution of the first substance in the Z-axis direction with reference to the first and second three-dimensional super-resolution images, and can more appropriately determine the disease status and the treatment policy.

Next, the procedure for acquiring the number of first substances will be described referring to FIG. 4 (*f*).

As shown in FIG. 4 (*f*), the processing part 111 classifies the coordinate points of the first three-dimensional super-resolution image into groups corresponding to the first substance. For example, the processing part 111 scans a predetermined reference space in a three-dimensional coordinate space, and determines whether the number of coordinate points included in the reference space is larger than a threshold value, and extracts the position of the reference space where the number of coordinate points is larger than the surroundings. Then, the processing part 111 classifies the group of the coordinate points included in the reference space at the extracted position into a group corresponding to one first substance as indicated by a broken line in FIG. 4 (f.)

Subsequently, the processing part 111 acquires the range of the nucleus in the three-dimensional space of the test cell. Specifically, the processing part 111 displaces the objective lens 36 in the Z-axis direction to acquire a third two-dimensional image based on the third fluorescent light at a plurality of different focus positions in the Z-axis direction. In the third two-dimensional image, the region in which the third fluorescent light is detected corresponds to the nucleus, and the region in which the third fluorescent light is not detected corresponds to outside the nucleus, that is, cytoplasm and the like. For each of the plurality of third two-dimensional images, the processing part 111 acquires the outline of the nucleus from the area where the third fluorescent light is detected. Then, the processing part 111 acquires the nucleus range in the three-dimensional coordinate space based on each focus position and the outline of the nucleus at the position.

Subsequently, the processing part 111 acquires the number of groups included in the nucleus range of the test cells in the three-dimensional coordinate space as the number of the first substance. Note that when a plurality of test cells are included in the first three-dimensional super-resolution image, the number of first substances can be determined, for example, by averaging the number of first substances acquired for each test cell. The processing part 111 similarly acquires the number of second substances based on the second three-dimensional super-resolution image.

The processing part 111 calculates the ratio of the number of the first substances and the number of the second substances acquired as described above, that is, "the number of the first substances/the number of the second substances". The ratio of the "number of first substances/number of second substances", for example, can be judged to be positive for breast cancer if it is larger than 2.2, negative for breast cancer if less than 1.8, and the boundary can be judged as 1.8 or more to 2.2 or less.

As described above, when the numbers of the first substance and the second substance are acquired based on the first and second three-dimensional images, "the number of the first substance/the number of the second substance" can be calculated with high accuracy. As a result, a judgment result with higher accuracy can be presented to a physician or the like.

Modification Example of Imaging Procedure

Figure 5:
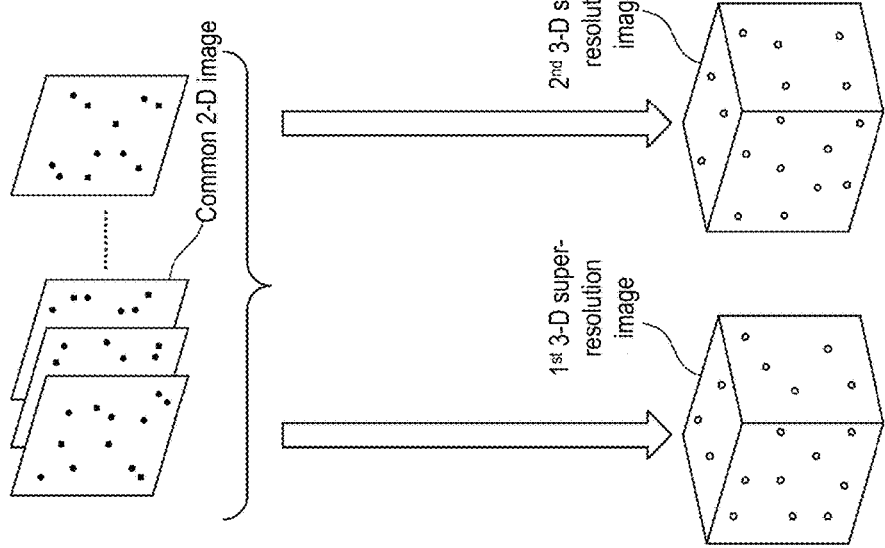
FIG. 5 (a) is a schematic view showing a first 3-dimensional super-resolution image obtained from a plurality of first 2-dimensional images, and a second 3-dimensional super-resolution image obtained from a plurality of second 2-dimensional images of the embodiment.
Figure 5:
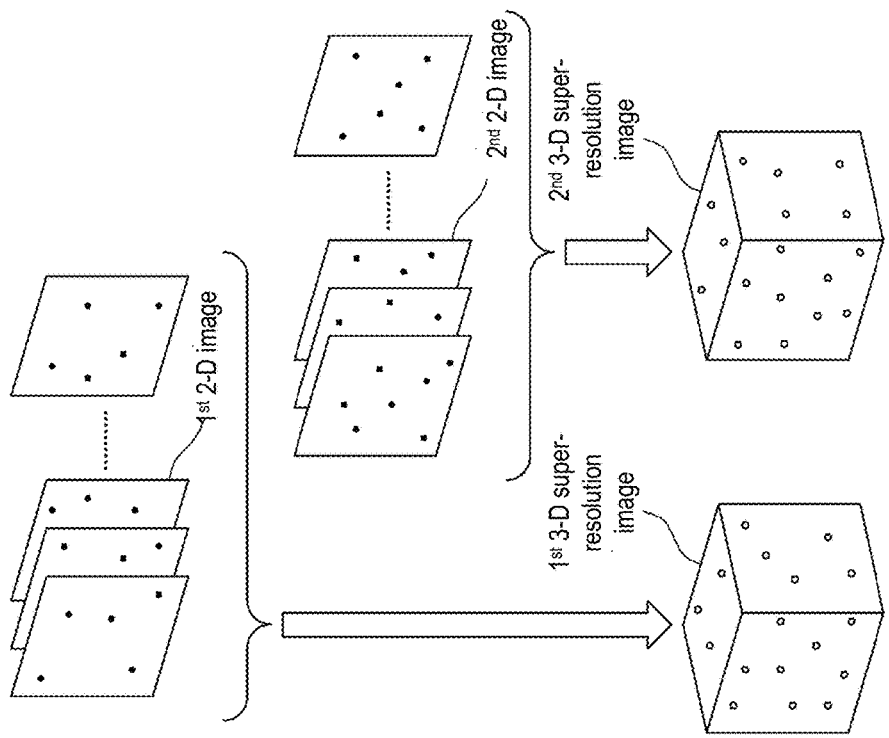

In the imaging procedure, the first fluorescent light and the second fluorescent light were captured separately by the imaging part 62. In this case, as shown in FIG. 5 (*a*), the processing part 111 acquires a plurality of second two-dimensional images after acquiring a plurality of first two-dimensional images. Then, the processing part 111 acquires the first three-dimensional super-resolution image based on the plurality of first two-dimensional images, and acquires the second three-dimensional super-resolution image based on the plurality of second two-dimensional images. In this way, when the first two-dimensional image and the second two-dimensional image are captured separately, the time required for capturing is lengthened.

In the imaging procedure, the first fluorescent light and the second fluorescent light also may be captured simultaneously by the imaging part 62. In this case, when the first and second fluorescent dyes are in the active state, the processing part 111 turns on the light sources 21 and 22 at the same time, and simultaneously irradiates the test cells with light from the light sources 21 and 22. In this way, the first fluorescent light and the second fluorescent light are given off simultaneously from the test cells, and the first fluorescent light and the second fluorescent light are simultaneously irradiated on the imaging surface 62*a* of the imaging part 62. As shown in FIG. 5 (*b*), the two-dimensional image acquired at this time is a common two-dimensional image in which the first two-dimensional image and the second two-dimensional image are superimposed. Note that in the case in which the first fluorescent light and the second fluorescent light are generated at the same time, the imaging part 62 is configured with a color CCD or the like.

Also in this case, as shown in FIG. 5 (*b*), the processing part 111 generates a first three-dimensional super-resolution image based on the first fluorescent light in the common two-dimensional image, and generates a second three-dimensional super-resolution image based on the second fluorescent light in the common two-dimensional image. When the first fluorescent light and the second fluorescent light are captured at the same time by the imaging part 62 in this way, the time required for imaging can be greatly shortened.

Preliminary Verification of Phase Modulation Mask

As described above, the phase modulation mask 50 is configured to be capable of coping with the first fluorescent light and the second fluorescent light having mutually different wavelengths. Note that phase modulation masks for appropriately forming an image according to a point spread function of one type of fluorescent light by generating a phase difference that is optimum for one kind of fluorescent light are generally known. Therefore, in order to make the phase modulation mask correspond to two types of fluorescent light, verification is performed by first modulating the phases of the first fluorescent light and the second fluorescent light with a phase modulation mask optimal for the first fluorescent light, and verification is performed by modulating the phases of the first fluorescent light and the second fluorescent light by a phase modulation mask optimal for the second fluorescent light.

As shown in FIG. 6 (a), the optical device 10 used in this verification differs from the configuration shown in FIG. 1 in that a polarizing plate 38 and a mirror 39 are provided instead of the beam expander 37, and a phase modulation device 51 is provided instead of the phase modulation mask 50. The polarizing plate 38 is configured by, for example, a polarization prism. The polarizing plate 38 is installed such that the polarization direction thereof is an appropriate polarization direction with respect to the phase modulation device 51. The mirror 39 reflects the fluorescent light passing through the polarizing plate 38 and guides it to the phase modulation device 51. The phase modulation mask used in this verification is a phase modulation device 51 for modulating the phase when reflecting incident light. The phase modulation device 51 is disposed on the Fourier plane of the optical system formed by the objective lens 36, the dichroic mirror 35, the polarizing plate 38, the mirror 39, and the condenser lens 61. Like the phase modulation mask 50 shown in FIG. 1, the phase modulation device 51 has the effect of modulating the point spread function on the imaging surface 62a.

As shown in FIG. 6 (b), the phase modulation device 51 includes a liquid crystal panel 51a. When the phase modulation device 51 is driven, the liquid crystal molecules 51b in the liquid crystal panel 51a rotate according to the setting, and the width of the liquid crystal molecules 51b changes in the incident direction of light. When the width of each liquid crystal molecule 51b varies in the light incident direction as described above, a difference in refractive index occurs according to the position in the incident region of the phase modulation device 51. In this way, the phase of the light incident on the liquid crystal panel 51a and reflected by the mirror 51c is modulated in accordance with the incident position.

When an image is input, the phase modulation device 51 sets the gradation of each pixel of the liquid crystal panel 51a based on the input image. The image input to the phase modulation device 51 holds information representing the gradation of each pixel of the phase modulation device 51. The phase modulation device 51 acquires the gradation to be set for each pixel from the input image and sets the rotation angle of each liquid crystal molecule 51b so that the gradation of each pixel becomes a desired gradation based on the input image. In this manner, the phase modulation device 51 sets the rotation angle of the liquid crystal molecules 51b based on the input image and sets the gradation pattern of each pixel. Note that in a case in which the phase modulation device 51 is configured to be capable of accepting other than images, the phase modulation device 51 selects each pixel of the liquid crystal panel 51a based on data other than the image holding information representing the gradation of each pixel of the phase modulation device 51.

In this verification, an "LCOS-SLM 01" manufactured by Hamamatsu Photonics KK was used as the phase modulation device 51. A first fluorescent bead and a second fluorescent bead were arranged on the slide glass 41 of the stage 40. When irradiated by the light from the light source 21, the first fluorescent bead generates fluorescent light having a central wavelength of 690 nm, that is, generates a first fluorescent light. When irradiated by the light from the light source 22, the second fluorescent bead generates fluorescent light having a central wavelength of 530 nm, that is, generates a second fluorescent light.

In this verification, when observing the first fluorescent light, the objective lens 36 is scanned in the Z axis direction with respect to the first fluorescent bead, and the position of the first fluorescent bead in the Z axis direction is relatively changed. Similarly, when observing the second fluorescent light, the objective lens 36 is scanned in the Z axis direction with respect to the second fluorescent bead, and the position of the second fluorescent bead in the Z axis direction is relatively changed. By scanning the objective lens 36 in the Z-axis direction in this way, it is possible to create a state similar to the state in which a plurality of fluorescent beads are arranged at different positions in the Z-axis direction. Then, the fluorescent light was imaged by the imaging part 62, and an image of the fluorescent light was acquired for each scanning position of the objective lens 3. 6

As shown in FIG. 6 (b), the liquid crystal panel 51a of the phase modulation device 51 is configured so that the phase can be modulated with 256 gradations per pixel by changing the tilt of the liquid crystal molecules 51b. The gradation of each pixel can be set from 0 to 255, and phase modulation of 256 gradations is realized by setting the gradation to any one of 0 to 255. The pattern distribution of the gradation set for all the pixels of the liquid crystal panel 51a is referred to as a "phase modulation pattern" hereinafter as a distribution for modulating the phase. That is, the distribution of the gradation set for each pixel of the liquid crystal panel 51a corresponds to the phase modulation pattern. The gradation of each pixel of the liquid crystal panel 51a is set by inputting an image to the phase modulation device 51 and setting a phase modulation pattern, and the fluorescent light entering the phase modulation device 51 changes in phase for each pixel, as shown in FIG. 6 (b).

The first phase modulation pattern shown in FIG. 7 (a) is a phase modulation pattern optimal for light of the first wavelength, that is, the first fluorescent light. The first phase modulation pattern imparts a first phase modulation to the light of the first wavelength, that is, the first fluorescent light. The second phase modulation pattern shown in FIG. 7 (b) is a phase modulation pattern optimal for light of the second wavelength, that is, the second fluorescent light. The second phase modulation pattern imparts a second phase modulation to the light of the second wavelength, that is, the second fluorescent light. When the phase modulation pattern of the phase modulation device 51 is set to the first phase modulation pattern, an image corresponding to the DH-PSF is formed on the imaging surface 62a for the first fluorescent light entering the phase modulation device 51. When the phase modulation pattern of the phase modulation device 51 is set to the second phase modulation pattern, an image corresponding to the DH-PSF is formed on the imaging surface 62a for the second fluorescent light entering the phase modulation device 51.

In FIGS. 7 (a) and 7 (b), pixels with a gradient of 0 are shown in black and pixels with a gradient of 255 are shown in white. Pixels of gradient 0 do not modulate the phase of the entering light. The phase of the first fluorescent light entering the pixel having the gradient of 255 is shifted by $2\pi$ from the phase of the first fluorescent light entering the pixel having the gradient of 0. The phase of the second fluorescent light entering the pixel having the gradient of 183 is shifted by $2\pi$ from the phase of the second fluorescent light entering the pixel having the gradient of 0.

In this verification and verification to be described later, in order to correct the aberration caused by the incident surface of the phase modulation device 51, a predetermined first correction mask was synthesized with the phase modulation pattern set in the phase modulation device 51 when the first fluorescent light enters the phase modulation device 51, and a predetermined second correction mask was synthesized with the phase modulation pattern set in the phase modulation device 51 when the second fluorescent light enters the phase modulation device 51. By synthesizing the first correction mask for a pixel whose gradient exceeds 255, the remaining value obtained by dividing the gradient by 256 was set as the gradient of the pixel. By synthesizing the second correction mask for a pixel whose gradient exceeds 183, the remaining value obtained by dividing the gradient by 184 was set as the gradient of the pixel.

The results of preliminary verification of the phase modulation device will be described with reference to FIGS. 8 (*a*) to 8 (*h*).

FIGS. 8 (*a*) and 8 (*b*) show the results of verification when the first phase modulation pattern is set in the phase modulation device 51 and the first fluorescent light is observed. In this case, as shown in FIG. 8 (*a*), the first fluorescent light is imaged on two points on the imaging surface 62*a*, and the straight line formed by the imaging positions of the two points is rotated 180 degrees by scanning the objective lens 36 in the Z axis direction. The relationship between the scanning position in the Z axis direction of the objective lens 36 and the angle of the straight line formed by the imaging positions of the two points is a one-to-one corresponding curve as shown in FIG. 8 (*b*). From the results in FIGS. 8 (*a*) and 8 (*b*), it was found that in this case an image corresponding to the DH-PSF of the first fluorescent light could be properly formed.

FIGS. 8 (*c*) and 8 (*d*) show the results of verification when the first phase modulation pattern is set in the phase modulation device 51 and the second fluorescent light is observed. In this case, the shape of DH-PSF collapsed depending on the position in the Z-axis direction as shown in FIG. 8 (*c*). Further, in the curve showing the relationship between the angle and the scanning position, a large step appears in part as shown in FIG. 8 (*d*). From the results in FIGS. 8 (*c*) and 8 (*d*), it was found that in this case an image corresponding to the DH-PSF of the second fluorescent light could not be properly formed.

FIGS. 8 (*e*) and 8 (*f*) show the results of verification when the second phase modulation pattern is set in the phase modulation device 51 and the first fluorescent light is observed. In this case, the shape of DH-PSF collapsed depending on the position in the Z-axis direction as shown in FIG. 8 (*e*). Also, as shown in FIG. 8 (*f*), the curve indicating the relationship between the scan position and the angle greatly collapsed, and the scan position and the angle did not correspond one to one. From the results in FIGS. 8 (*e*) and 8 (*f*), it was found that in this case an image corresponding to the DH-PSF of the first fluorescent light could not be properly formed.

FIGS. 8 (*g*) and 8 (*h*) show the results of verification when the second phase modulation pattern is set in the phase modulation device 51 and the second fluorescent light is observed. In this case, the two bright spot images become appropriate as shown in FIG. 8 (*g*). Also, as shown in FIG. 8 (*h*), the relationship between the angle and the scan position was a one-to-one curve. From the results in FIGS. 8 (*g*) and 8 (*h*), it was found that in this case an image corresponding to the DH-PSF of the second fluorescent light could be properly formed.

From the results of FIGS. 8 (*a*), 8 (*b*), 8 (*g*) and 8 (*h*), it was found that the combination of setting the phase modulation pattern of the phase modulation device 51 and the center wavelength of fluorescent light incident on the phase modulation device 51 is optimum in some cases, such that an image corresponding to fluorescent DH-PSF could be properly formed. This can be said to be appropriate as a result. On the other hand, it was found that the combination of setting the phase modulation pattern of the phase modulation device 51 and the center wavelength of fluorescent light incident on the phase modulation device 51 is not optimum in some cases, such that an image corresponding to fluorescent DH-PSF could not be properly formed. From this, it was found that it is necessary to appropriately select the setting of the phase modulation pattern of the phase modulation device 51 and the fluorescent light incident on the phase modulation device 51.

Based on the above results, the inventors considered the integration of a first phase modulation pattern optimum for the first fluorescent light and a second phase modulation pattern optimum for the second fluorescent light so as to correspond to both the first fluorescent light and the second fluorescent light. At that time, the inventors focused on overlapping wavelength bands of the first fluorescent light and the second fluorescent light. The first fluorescent light is light having an intensity peak at a first wavelength and the second fluorescent light is light having an intensity peak at a second wavelength. That is, the wavelength band of the first fluorescent light spreads to some extent with the first wavelength as the center wavelength, and the wavelength band of the second fluorescent light spreads to certain extent with the second wavelength as the central wavelength. Then, a part of the wavelength band of the first fluorescent light and a part of the wavelength band of the second fluorescent light overlap each other.

The inventors have found that when a part of the wavelength band of the first fluorescent light and a part of the wavelength band of the second fluorescent light overlap, an image corresponding to the DH-PSF of the first fluorescent light and the second fluorescent light can be appropriately formed by an integrated phase modulation pattern if the first phase modulation pattern optimal for the first fluorescent light and the second phase modulation pattern optimum for the second fluorescent light are integrated as described below. The phase modulation patterns of examples 1 to 6 described below are examples in which the first phase modulation pattern and the second phase modulation pattern are integrated by various methods. The inventors also verified whether the image corresponding to the DH-PSF of the first fluorescent light and the second fluorescent light is appropriately formed by the phase modulation pattern of examples 1 to 6.

Phase Modulation Pattern of Example 1

The phase modulation pattern of the example 1 is produced by combining the first phase modulation pattern and the second phase modulation pattern at a predetermined ratio for each position. In the case of synthesizing the first phase modulation pattern and the second phase modulation pattern by a:b, the gradient of the phase modulation pattern of the first example is calculated based on the first gradient of the first phase modulation pattern and the second gradient of the second phase modulation pattern, as represented in the equation below.

Gradient of phase modulation pattern of example 1=(first gradient $xa$+second gradient $xb$)/($a+b$)

(where a and b are both positive real numbers)

Specifically, when using the phase modulation pattern of example 1, an image corresponding to the phase modulation pattern of example 1 is produced, the produced image is input to the phase modulation device 51, and the phase modulation pattern of example 1 is realized in the modulation device 51 based on the input image. The gradient in each pixel of the image corresponding to the phase modulation pattern of example 1 is set to a gradient between the gradient of light of the first wavelength and the gradient of light of the second wavelength. That is, the gradient is calculated by the above equation based on the gradient at the same pixel position of the first phase modulation pattern that is optimal for the first fluorescent light and the gradient at the same pixel position of the second phase modulation pattern that is optimal for the second fluorescent light. The phase modulation pattern of example 1 is set in the phase modulation device 51, and the rotation angle of each molecule 51b of the liquid crystal panel 51a is set by inputting the image corresponding to the phase modulation pattern produced in example 1 to the phase modulation device 51.

Figure 9:
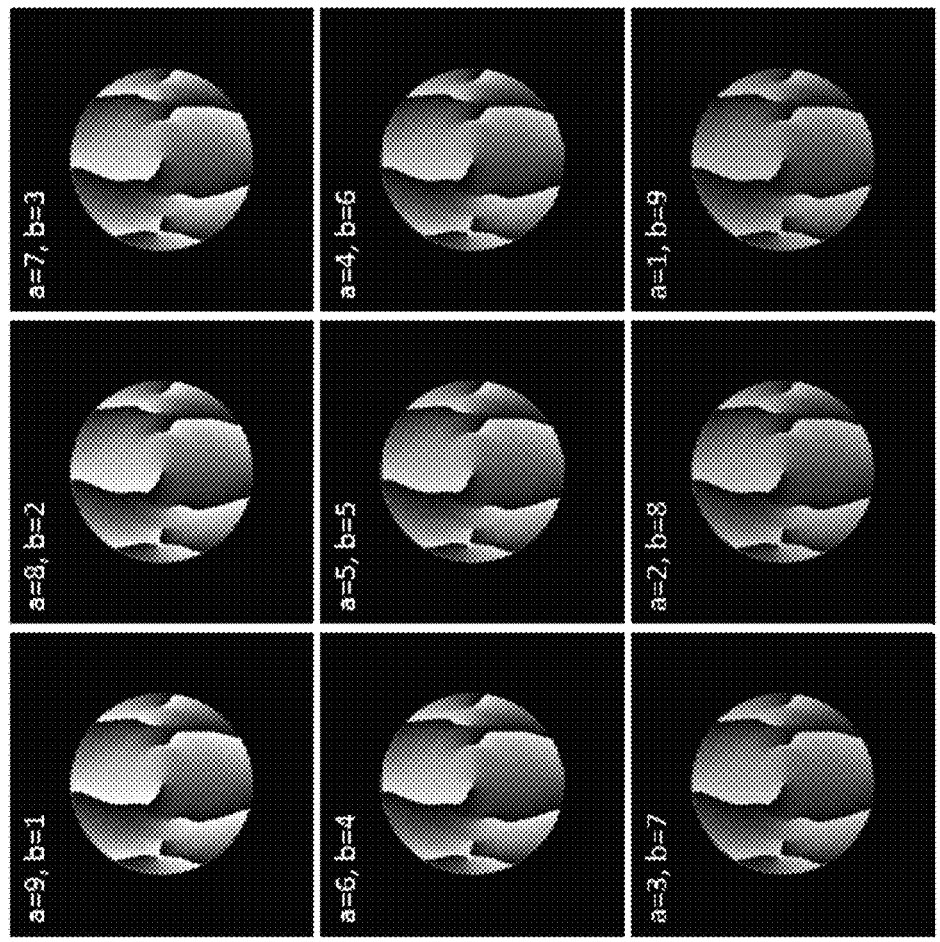
FIG. 9 shows the structure of a phase modulation pattern of example 1.

FIG. 9 is a diagram showing the phase modulation pattern of example 1 when (a, b)=(9, 1), (8, 2), (7, 3), (6, 4), (5, 5), (4, 6), (3, 7), (2, 8) and (1, 9), respectively. The results of verification of these nine phase modulation patterns are shown below.

Figure 10:
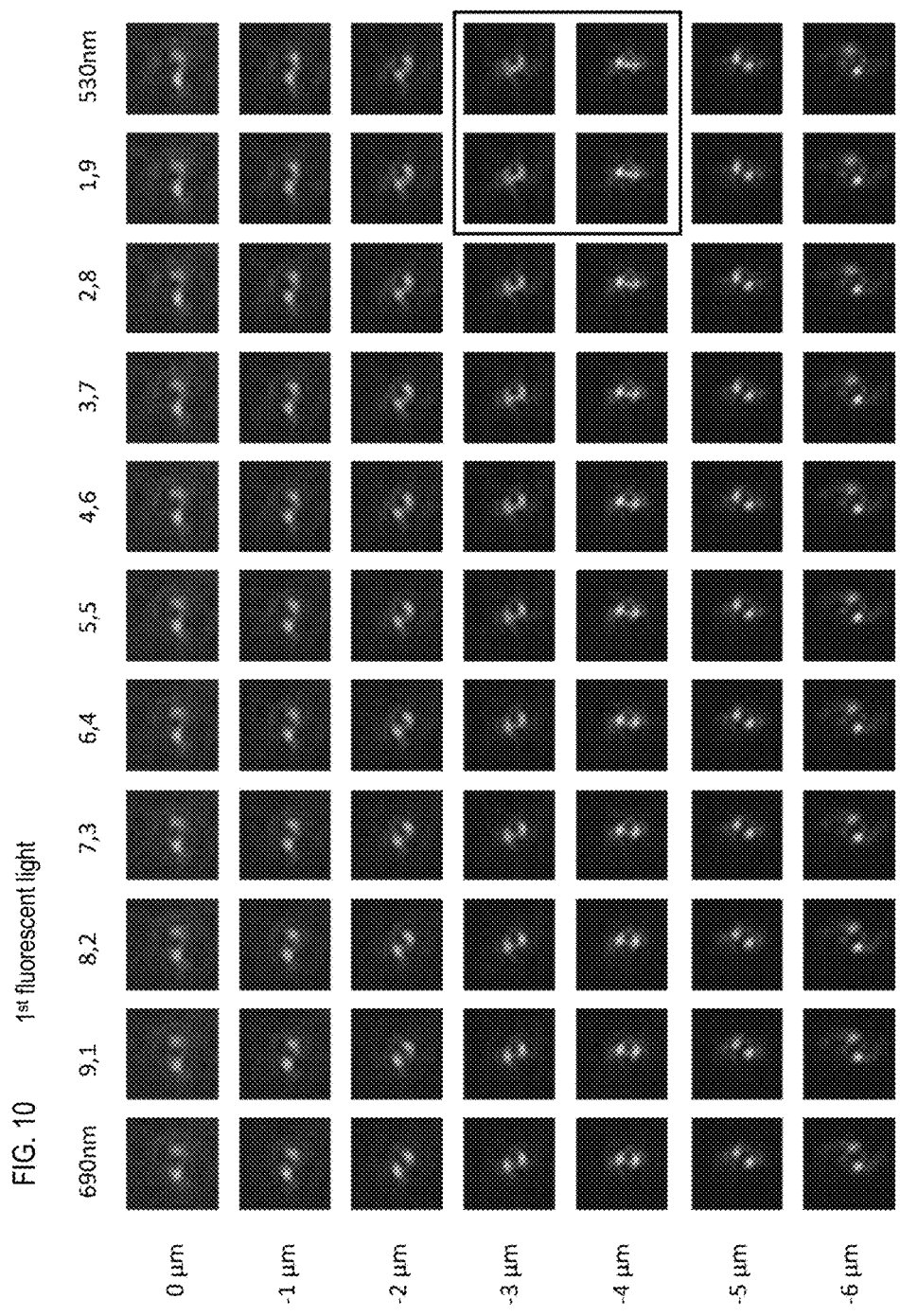
FIG. 10 shows the imaging state of the first fluorescent light using the phase modulation pattern of example 1.

FIG. 10 shows the image forming status of the first fluorescent light on the imaging surface 62a when the first fluorescent light is observed using the nine types of phase modulation pattern of example 1 above, the first phase modulation pattern, and the second phase modulation pattern. The vertical direction indicates the scanning position of the objective lens 36. The leftmost "690 nm" and the rightmost "530 nm" indicate the case of using the first phase modulation pattern and the second phase modulation pattern, respectively.

As shown in FIG. 10, at each of the scan positions, a bright spot image corresponding to the DH-PSF was observed in a blurred condition progressing to the right, that is, as the blending ratio of the second phase modulation pattern rises and the phase modulation pattern approaches the second phase modulation pattern. Also, when the scan position is −3 μm or −4 μm progressing to the right, a new bright spot based on the zero order light appears between the two bright spots. In particular, when using the phase modulation pattern of (a, b)=(1, 9) and the second phase modulation pattern, the intensity of the bright spot of the bright spot image of the zero order light was higher compared to the bright spot image corresponding to DH-PSF as shown in the area surrounded by a solid line frame. In such a case, there is a possibility that a curve indicating the relationship between the scan position and the angle, and a three-dimensional super-resolution image cannot be properly generated by erroneously recognizing the zero order light as the bright spot of the DH-PSF.

Figure 11:
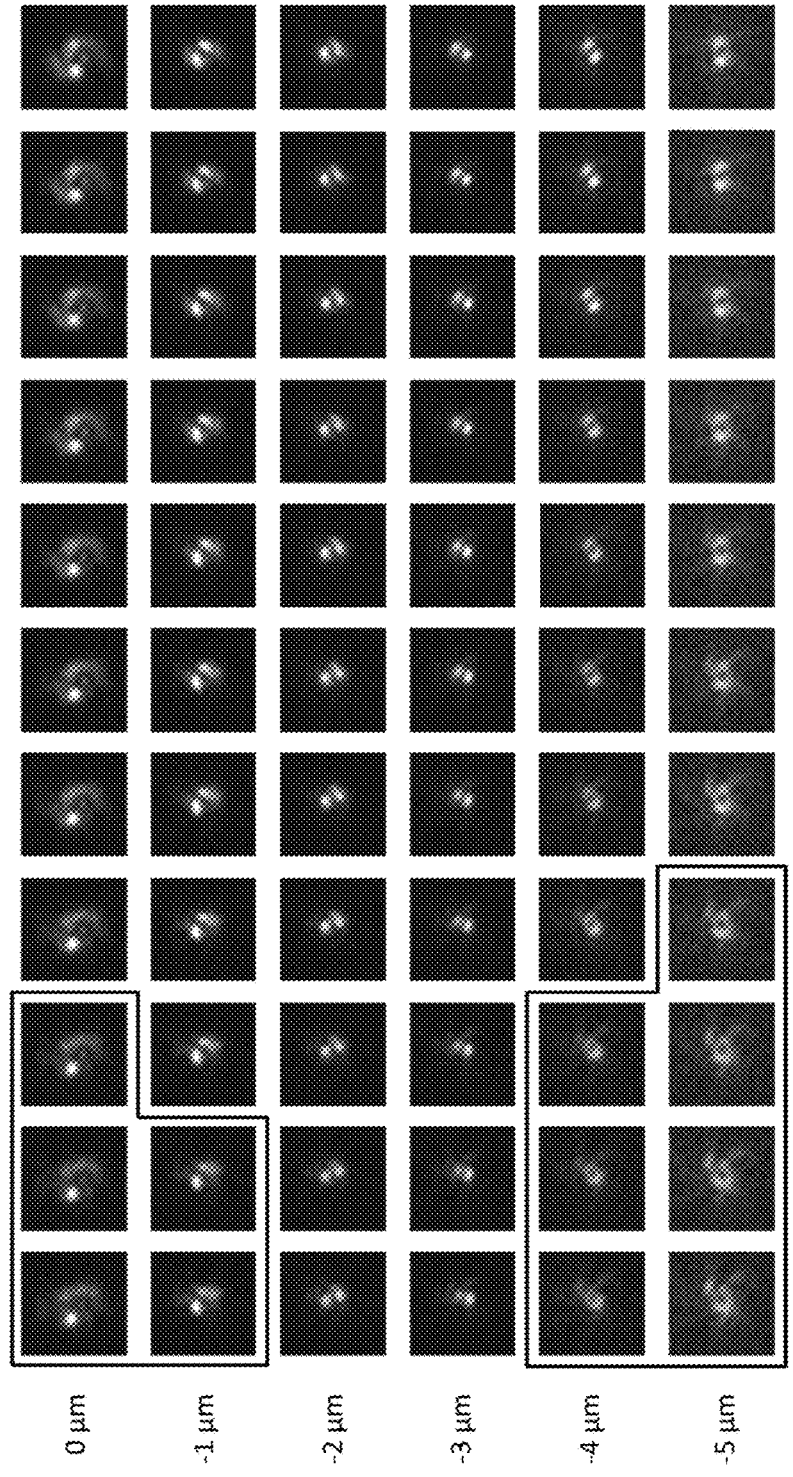
FIG. 11 shows the imaging state of the second fluorescent light using the phase modulation pattern of example 1.

FIG. 11 shows the image forming status of the second fluorescent light on the imaging surface 62a when the second fluorescent light is observed using the nine types of phase modulation pattern of example 1 above, the first phase modulation pattern, and the second phase modulation pattern.

As shown in FIG. 11, at each of the scan positions, a bright spot image corresponding to the DH-PSF was observed in a blurred condition progressing to the left, that is, as the blending ratio of the first phase modulation pattern rises and the phase modulation pattern approaches the first phase modulation pattern. In particular, when using the phase modulation pattern of (a, b)=(9, 1), (8,2), (7,3) and the first phase modulation pattern, the number of bright spots was greater than two spots depending on the scan position as indicated in the area surrounded by the solid line frame.

From the results of FIGS. 10 and 11, it was understood that an image corresponding to DH-PSF of both the first fluorescent light and the second fluorescent light can be properly formed when the phase modulation pattern of example 1 was set at (a, b)=(6, 4), (5, 5), (4, 6), (3, 7), and (2, 8).

Further, the verification result in the case where the phase modulation pattern of example 1 was set with (a, b)=(5, 5) will be described with reference to FIGS. 12 (a) to 12 (d).

FIGS. 12 (a) and 12 (b) show the results when observing the first fluorescent light, and FIGS. 12 (c) and (d) show the results when observing the second fluorescent light. As shown in FIGS. 12 (a) and 12 (c), the image corresponding to the DH-PSF of both the first fluorescent light and the second fluorescent light can be appropriately formed when the slope of the straight line formed by the two imaging positions is in the range of −90 degrees to +90 degrees. Also, as shown in FIGS. 12 (b) and 12 (d), the relationship between the angle and the scan position was a one-to-one curve.

From the above verification results, it was found that an image corresponding to DH-PSF of both the first fluorescent light and the second fluorescent light can be properly formed by the phase modulation pattern of example 1 when the phase modulation pattern of example 1 is set in the phase modulation device 51 if the first phase modulation pattern and the second phase modulation pattern are combined at a predetermined ratio as the phase modulation pattern of example 1. Note that, similarly for three or more kinds of fluorescent lights having different center wavelengths, an image corresponding to DH-PSF of the three fluorescent lights can be appropriately formed by synthesizing optimal phase modulation patterns for the three types of fluorescent lights at a predetermined ratio.

Next, the synthesis of the first phase modulation pattern and the second phase modulation pattern as described above will be described in detail with reference to FIGS. 13 (a) to 13 (c). FIG. 13 (a) through 13 (c) schematically show one pixel position on a liquid crystal panel 51a in the first phase modulation pattern, second phase modulation pattern, and the phase modulation pattern of example 1, respectively. In FIGS. 13 (a) to 13 (c), it is assumed for the sake of convenience that the gradient of one pixel is set by one liquid crystal molecule 51 b.

In order to appropriately form an image corresponding to the DH-PSF based on the first fluorescent light, the distance by which the first fluorescent light incident on a predetermined pixel position reciprocates through the liquid crystal molecules 51b is set as a first distance L1, as shown in FIG. 13 (a). Similarly, in order to appropriately form an image corresponding to the DH-PSF based on the second fluorescent light, the distance by which the second fluorescent light incident on a predetermined pixel position reciprocates through the liquid crystal molecules 51b is set as a second distance L2, as shown in FIG. 13 (b). The magnitude at which the phase of the first fluorescent light is modulated by the first distance L1 is equal to the magnitude at which the phase of the second fluorescent light is modulated by the second distance L2. That is, when considering the wavelength of the first fluorescent light, the wavelength of the second fluorescent light, and the refractive index of the liquid crystal molecules 51b, the optical path length of the first fluorescent light based on the first distance L1 and the optical path length of the second fluorescent light based on the second distance L2 are equal to each other.

In order to appropriately form an image corresponding to the DH-PSF based on both the first fluorescent light and the second fluorescent light, the distance by which the first fluorescent light and second fluorescent light incident on a predetermined pixel position reciprocate through the liquid crystal molecules 51b is set as a third distance L3, as shown in FIG. 13 (c). At this time, the third distance L3 is set between the first distance and the second distance. That is, the magnitude of the phase modulation at each position of the phase modulation pattern of example 1 is set to a magnitude between the magnitude of the phase modulation in the first phase modulation pattern and the magnitude of the phase modulation in the second phase modulation pattern. Specifically, similar to the equation of the phase modulation pattern of example 1 described above, the third distance L3 is calculated by the following equation.

Third distance $L3 = (\text{first distance } L1 \times a + \text{second distance } L2 \times b)/(a+b)$ When the phase modulation pattern of example 1 is set, the setting as shown in FIG. 13 (c) is performed at all pixel positions. In this way the phase modulation pattern of example 1 can appropriately for an image corresponding to the DH-PSF of both the first fluorescent light and the second fluorescent light.

Note that when $(a, b)=(5, 5)$, the third distance L3 is set between the first distance L1 and the second distance L2. In this case, phase modulation occurs of a magnitude intermediate to the magnitude of phase-modulating the first fluorescent light by the first phase modulation pattern and the magnitude of phase-modulating the first fluorescent light by the second phase modulation pattern. For the second fluorescent light, phase modulation occurs of a magnitude intermediate to the magnitude of phase-modulating the second fluorescent light by the first phase modulation pattern and the magnitude of phase-modulating the second fluorescent light by the second phase modulation pattern.

Phase Modulation Pattern of Example 2

As shown in FIG. 14 (a), the phase modulation pattern of example 2 is produced by disposing the first phase modulation pattern and the second phase modulation pattern in a mosaic pattern. In the phase modulation pattern of example 2, the region group obtained by dividing the incident region into a large number is divided into a first region composed of a light gray region and a second region composed of a dark gray region. Each region of the first region and each region of the second region are adjacent to each other. The first phase modulation pattern is set in the light gray region, and the second phase modulation pattern is set in the dark gray region. In the phase modulation pattern of example 2, one region of the first region and one region of the second region have a square shape of M pixels on a side.

That is, the phase modulation pattern of example 2 is a phase modulation pattern that includes the region for imparting the first phase modulation to the light of the first wavelength, that is, the first region in which the first phase modulation pattern is set, and a second region in which the second phase modulation pattern is set for imparting the second phase modulation to the light of the second wavelength. In other words, in a certain region of the incident region within the phase modulation pattern of the second embodiment, the distance traveled by the light flux incident on the first region for phase modulation is set to the first distance L1 shown in FIG. 13 (a), and the distance that the light flux entering the second region travels for phase modulation is set to the second distance L2 shown in FIG. 13 (b).

FIGS. 14 (b) to 14 (d) are diagrams showing the phase modulation pattern of example 2 when M=1, 3, and 5, respectively. In FIGS. 14 (b) to 14 (d), the arrangement of the first phase modulation pattern and the second phase modulation pattern in the vicinity of the center is enlarged and displayed. The results of verification of these three phase modulation patterns are shown below.

FIGS. 15 (a) to 15 (d) are diagrams showing the results of fluorescent light observation using the phase modulation pattern of example 2 with M=1. As shown in FIGS. 15 (a) and 15 (b), the two bright spot images became appropriate, and the relationship between the scan position and the angle also became a one-to-one curve when observing the first fluorescent light. As shown in FIGS. 15 (c) and 15 (d), the two bright spot images became appropriate, and the relationship between the scan position and the angle also became a one-to-one curve when observing the second fluorescent light. Therefore, an image corresponding to the DH-PSF of both the first fluorescent light and the second fluorescent light can be appropriately formed by using the phase modulation pattern of example 2 with M=1.

FIGS. 15 (e) and 15 (f) show the results of observing the first fluorescent light and second fluorescent light using the phase modulation pattern of example 2 with M=5. In this case as well as in the case where the first fluorescent light was observed and the case where the second fluorescent light was observed, the two bright spot images were appropriate. Therefore, an image corresponding to the DH-PSF of both the first fluorescent light and the second fluorescent light can be appropriately formed by using the phase modulation pattern of example 2 with M=5.

FIG. 16 (a) shows the result of observing the first fluorescent light with a wide field of view using the phase modulation pattern of example 2 with M=1 and 3. FIG. 16 (b) shows the result of observing the second fluorescent light with a wide field of view using the phase modulation pattern of example 2 with M=1 and 3. In FIGS. 16 (a) and 16 (b), the upper row is an image generated by the imaging part 62 when fluorescent light is directly observed. The lower row is the image with the contrast of the upper image adjusted. In FIGS. 16 (a) and 16 (b), the image on the left side corresponds to the phase modulation pattern with M=1 and the image on the right side corresponds to the phase modulation pattern with M=3.

In the images of the lower row in FIGS. 16 (a) and 16 (b), bright spots appear at positions indicated by arrows. The luminescent spot is a bright spot based on the diffracted light generated by the first phase modulation pattern and the second phase modulation pattern being periodically arranged in a mosaic pattern. Since the diffraction angle is smaller as the value of M is larger, the diffraction light appears in a region closer to the center of the image in the case of using the phase modulation pattern with M=3 than in the case of using the phase modulation pattern with M=1. In the case of M=3, it was found that the diffracted light was superimposed on a part of the bright spot corresponding to the DH-PSF which was desired originally.

Therefore, when using the phase modulation pattern of example 2, it can be said that it is desirable to make the value of M as small as possible. However, when the size of one pixel of the phase modulation device 51 is small, the diffracted light may not enter the field of view even if the value of M is increased. Also, since the bright spot of the diffracted light is darker than the bright spot corresponding to the DH-PSF that is desired, it may not be a problem particularly when calculating three-dimensional coordinates based on the rotational angle. The value of M that can appropriately form an image corresponding to DH-PSF of two kinds of fluorescent lights having different central wavelengths is not limited to 1, 3, and 5 as described above.

Phase Modulation Pattern of Example 3

As shown in FIG. 17 (a), the phase modulation pattern of example 3 is produced by disposing the first phase modulation pattern and the second phase modulation pattern in a mosaic pattern similar to the phase modulation pattern of example 2. However, in the phase modulation pattern of example 3, one region of the first region and one region of the second region are both rectangular shapes of M pixels in the vertical direction and N pixels in the horizontal direction.

FIGS. 17 (b) to 17 (d) are diagrams showing the phase modulation pattern of example 3 when (M,N)=(1,2), (1,4), (1,32), respectively. The results of verification of these three phase modulation patterns are shown below.

FIGS. 18 (a) to 18 (d) are diagrams showing the results of fluorescent light observation using the phase modulation pattern of example 3 with (M,N)=(1,2). As shown in FIGS. 18 (a) and 18 (b), the two bright spot images became appropriate, and the relationship between the scan position and the angle also became a one-to-one curve when observing the first fluorescent light. As shown in FIGS. 18 (c) and 18 (d), the two bright spot images became appropriate, and the relationship between the scan position and the angle also became a one-to-one curve when observing the second fluorescent light. Therefore, an image corresponding to the DH-PSF of both the first fluorescent light and the second fluorescent light can be appropriately formed by using the phase modulation pattern of example 3 with (M,N)=(1,2).

FIGS. 18 (e) and 18 (f) show the results of observing the first fluorescent light and second fluorescent light using the phase modulation pattern of example 3 with (M,N)=(1,32). In this case also the two bright spot images were appropriate when observing the first fluorescent light and when observing the second fluorescent light. Therefore, an image corresponding to the DH-PSF of both the first fluorescent light and the second fluorescent light can be appropriately formed by using the phase modulation pattern of example 3 with (M,N)=(1,32).

FIG. 19 (a) shows the result of observing the first fluorescent light with a wide field of view using the phase modulation pattern of example 3 with (M,N)=(1,2), (1,4). FIG. 19 (a) shows the result of observing the second fluorescent light with a wide field of view using the phase modulation pattern of example 3 with (M,N)=(1,2), (1,4). In FIGS. 19 (a) and 19 (b), the image on the left side corresponds to the phase modulation pattern with (M,N)=(1,2) and the image on the right side corresponds to the phase modulation pattern with (M,N)=1,4).

In the lower row images of FIGS. 19 (a) and 19 (b), bright spots appear at positions indicated by arrows similar to the case shown in FIGS. 16 (a) and 16 (b). The vertical direction and the horizontal direction in FIG. 17 (a) correspond to the horizontal direction and the vertical direction, respectively, in the images of FIGS. 19 (a) and 19 (b). In this verification, since the value of M is fixed at 1, diffracted light appears at the same position on both ends in the left-right direction as shown in the lower row images of FIGS. 19 (a) and 19 (b). On the other hand, as the value of N increases, the diffracted light approaches the center of the image in the vertical direction while maintaining the position in the horizontal direction. It is assumed that the diffracted light approaches the center of the image in the left-right direction when the value of M increases from 1 toward 2 as can be seen from the verification of the phase modulation pattern of example 2, even when using the rectangular phase modulation patter of example 3 under the condition of (M,N)=(2,4).

Therefore, when using the phase modulation pattern of example 3, it can be said that it is desirable to make the value of M,N as small as possible. Note that the value of M,N that can appropriately form an image corresponding to DH-P SF of two kinds of fluorescent lights having different central wavelengths is not limited to (1,2), (1,4), (1,32) as described above.

Phase Modulation Pattern of Example 4

As shown in FIG. 20 (a), the phase modulation pattern of example 4 is produced by disposing the first phase modulation pattern and the second phase modulation pattern in a stripe pattern. One region of the first region and one region of the second region are formed in a stripe shape of M pixels in the horizontal direction. Each region of the first region and each region of the second region extend from one end to the other end of the incident region where the first fluorescent light and the second fluorescent light enter. That is, the length in the vertical direction is set to be the maximum pixel value of the settable length.

FIGS. 20 (b) to 20 (d) are diagrams showing the phase modulation pattern of example 4 when M=1, 2, and 16, respectively. The results of verification of these three phase modulation patterns are shown below.

FIGS. 21 (a) to 21 (d) are diagrams showing the results of fluorescent light observation using the phase modulation pattern of example 4 with M=1. As shown in FIGS. 21 (a) and 21 (b), the two bright spot images became appropriate, and the relationship between the scan position and the angle also became a one-to-one curve when observing the first fluorescent light. As shown in FIGS. 21 (c) and 21 (d), the two bright spot images became appropriate, and the relationship between the scan position and the angle also became a one-to-one curve when observing the second fluorescent light. Therefore, an image corresponding to the DH-PSF of both the first fluorescent light and the second fluorescent light can be appropriately formed by using the phase modulation pattern of example 4 with M=1.

FIGS. 21 (e) and 21 (f) show the results of observing the first fluorescent light and second fluorescent light using the phase modulation pattern of example 4 with M=16. In this case also the two bright spot images were appropriate when observing the first fluorescent light and when observing the second fluorescent light. Therefore, it is understood that an image corresponding to the DH-PSF of both the first fluorescent light and the second fluorescent light can be appropriately formed by using the phase modulation pattern of example 4 with M=16.

FIG. 22 (a) shows the result of observing the first fluorescent light with a wide field of view using the phase modulation pattern of example 4 with M=1 and 2. FIG. 22 (b) shows the result of observing the second fluorescent light with a wide field of view using the phase modulation pattern of example 4 with M=1 and 2. In FIGS. 22 (a) and 22 (b), the image on the left side corresponds to the phase modulation pattern with M=1 and the image on the right side corresponds to the phase modulation pattern with M=2.

In the lower row images of FIGS. 22 (a) and 22 (b), bright spots appear at positions indicated by arrows similar to the case shown in FIGS. 16 (a) and 16 (b). However, unlike the case of the phase modulation pattern of example 2, diffracted light appeared only in the vertical direction as shown in the lower row images of FIGS. 22 (a) and 22 (b). On the other hand, as the value of M increases, the diffracted light approaches the center of the image in the vertical direction similarly to the phase modulation pattern of example 2.

Therefore, when using the phase modulation pattern of example 4, it can be said that it is desirable to make the value of M as small as possible. Note that The value of M that can appropriately form an image corresponding to DH-P SF of two kinds of fluorescent lights having different central wavelengths is not limited to 1, 2, and 16 as described above.

Phase Modulation Pattern of Example 5

As shown in FIG. 23 (a), the phase modulation pattern of example 5 is produced by disposing the first phase modulation pattern and the second phase modulation pattern in a concentric pattern. In other words, each region of the first region and each region of the second region are concentric ring shapes. Note that the center of each region of the first region and the center of each region of the second region also may be displaced. One region of the first region and one region of the second region are arranged so as to be interchanged at every M pixel interval from the center.

FIGS. 23 (b) to 23 (e) are diagrams showing the phase modulation pattern of example 5 when M=1, 2, 5, and 60, respectively. The results of verification of these four phase modulation patterns are shown below.

FIGS. 24 (a) to 24 (d) are diagrams showing the results of fluorescent light observation using the phase modulation pattern of example 5 with M=1. As shown in FIGS. 24 (a) and 24 (b), the two bright spot images became appropriate, and the relationship between the scan position and the angle also became a one-to-one curve when observing the first fluorescent light. As shown in FIGS. 24 (c) and 24 (d), the two bright spot images became appropriate, and the relationship between the scan position and the angle also became a one-to-one curve when observing the second fluorescent light. Therefore, an image corresponding to the DH-PSF of both the first fluorescent light and the second fluorescent light can be appropriately formed by using the phase modulation pattern of example 5 with M=1.

FIGS. 24 (e) and 24 (f) show the results of observing the first fluorescent light and second fluorescent light using the phase modulation pattern of example 5 with M=5. In this case also the two bright spot images were appropriate when observing the first fluorescent light and when observing the second fluorescent light. Therefore, it was understood that an image corresponding to the DH-PSF of both the first fluorescent light and the second fluorescent light can be appropriately formed by using the phase modulation pattern of example 5 with M=5.

FIGS. 24 (g) and 24 (h) show the results of observing the first fluorescent light and second fluorescent light using the phase modulation pattern of example 5 with M=60. In this case the two bright spot images were collapsed when observing the first fluorescent light and when observing the second fluorescent light. Therefore, it was found that when the value of M becomes too large, it is impossible to properly form an image corresponding to the DH-PSF of the first fluorescent light and the second fluorescent light.

FIG. 25 (a) shows the result of observing the first fluorescent light with a wide field of view using the phase modulation pattern of example 5 with M=2 and 5. FIG. 25 (b) shows the result of observing the second fluorescent light with a wide field of view using the phase modulation pattern of example 5 with M=2 and 5. In FIGS. 25 (a) and 25 (b), the image on the left side corresponds to the phase modulation pattern with M=2 and the image on the right side corresponds to the phase modulation pattern with M=5.

In the lower row images of FIGS. 25 (a) and 25 (b), ring-shaped diffracted light surrounding the bright spot image appears as indicated by an arrow. Referring to the image of the lower row of M=2 and 5, this diffracted light appeared as ring-shaped diffracted light having a smaller diameter as the value of M increases, and approached the bright spot corresponding to the DH-PSF originally desired. Therefore, when using the phase modulation pattern of example 5, it can be said that it is desirable to make the value of M as small as possible. The value of M that can appropriately form an image corresponding to DH-PSF of two kinds of fluorescent lights having different central wavelengths is not limited to 1, 2, and 5 as described above.

According to the phase modulation pattern of example 5, the brightness of the diffracted light is dispersed in a wider range along the circle as compared with the phase modulation pattern of example 2 through example 4, so that the luminance of the diffracted light decreases. Therefore, in the case of using the phase modulation pattern of example 5, a serious problem does not occur even if the diffracted light overlaps the bright spot corresponding to the DH-PSF originally desired. From this, the phase modulation pattern of example 5 in which the value of M is small differs from the phase modulation pattern of example 2 to example 4 in that it can be said that an image corresponding to DH-PSF of both the first fluorescent light and the second fluorescent light can be appropriately formed.

Phase Modulation Pattern of Example 6

The phase modulation pattern of example 6 is produced by arranging the first phase modulation pattern and the second phase modulation pattern, in which the positions, sizes and the like are modified, are arranged in a mosaic pattern of a square shape similarly to the phase modulation pattern of the example 2.

FIG. 26 shows eight types of the phase modulation pattern of example 5. "MosaicROTATE5" is a phase modulation pattern in which a first phase modulation pattern rotated 5 degrees around the center and a second phase modulation pattern are arranged in a mosaic pattern. "MosaicROTATE30" is a phase modulation pattern in which a first phase modulation pattern rotated 30 degrees around the center and a second phase modulation pattern are arranged in a mosaic pattern. "MosaicSHIFT5" is a phase modulation pattern in which a first phase modulation pattern shifted by 5 pixels in the right direction and a second phase modulation pattern shifted by 5 pixels in the left direction are arranged in a mosaic pattern. "MosaicSHIFT10" is a phase modulation pattern in which a first phase modulation pattern shifted by 10 pixels in the right direction and a second phase modulation pattern shifted by 10 pixels in the left direction are arranged in a mosaic pattern.

"MosaicEXPAND10" is a phase modulation pattern in which a first phase modulation pattern has a diameter enlarged by 10 pixels and a second phase modulation pattern are arranged in a mosaic pattern. "MosaicEXPAND40" is a phase modulation pattern in which a first phase modulation pattern has a diameter enlarged by 40 pixels and a second phase modulation pattern are arranged in a mosaic pattern. "MosaicREDUCE20" is a phase modulation pattern in which a first phase modulation pattern has a diameter reduced by 20 pixels and a second phase modulation pattern are arranged in a mosaic pattern. "MosaicREDUCE40" is a phase modulation pattern in which a first phase modulation pattern has a diameter reduced by 40 pixels and a second phase modulation pattern are arranged in a mosaic pattern. The results of verification of these eight phase modulation patterns are shown below.

FIGS. 27 (a) and 27 (b) show the results of observation of fluorescent light using "mosaicROTATE5". In this case the two bright spot images were appropriate when observing the first fluorescent light and when observing the second fluorescent light. FIGS. 27 (c) and 27 (d) show the results of observation of fluorescent light using "mosaicROTATE30". In this case the two bright spot images were collapsed when observing the first fluorescent light and when observing the second fluorescent light. Therefore, it was found that when the difference between the rotation angle of the first phase modulation pattern and the rotation angle of the second phase modulation pattern becomes large, it is impossible to appropriately form an image corresponding to the DH-PSF of the first fluorescent light and the second fluorescent light.

FIGS. 27 (e) and 27 (f) show the results of observation of fluorescent light using "mosaicSHIFT5". In this case, FIGS. 27 (g) and 27 (h) show the results of observing fluorescent light using "mosaicSHIFT10" when observing the first fluorescent light and when observing the second fluorescent light. In this case, the two bright spot images were appropriate in the case of observing the first fluorescent light and the case of observing the second fluorescent light, but the bright spot image slightly collapsed as compared with "mosaicSHIFT5".

Note that the reason the bright point image of "mosaicSHIFT10" is slightly distorted compared to "mosaicSHIFT5" is obvious when considering the case where the fluorescent light of the center wavelength is incident on the optimal phase modulation pattern for only one center wavelength. That is, even if the fluorescent light incident on the phase modulation pattern is the optimal fluorescent light for the phase modulation pattern, the shape of the bright spot image collapses as the center of the incident beam moves away from the center of the phase modulation pattern. Therefore, in "mosaicSHIFT10" in which there is a large shift from the center, the bright spot image tends to collapse.

FIGS. 28 (a) and 28 (b) show the results of observation of fluorescent light using "mosaicEXPAND10". In this case the two bright spot images were appropriate when observing the first fluorescent light and when observing the second fluorescent light. FIGS. 28 (c) and 28 (d) show the results of observation of fluorescent light using "mosaicEXPAND40". In this case, the two bright spot images were appropriate in the case of observing the first fluorescent light and the case of observing the second fluorescent light, but the bright spot image slightly collapsed as compared with "mosaicEXPAND10".

Note that the reason the bright point image of "mosaicEXPAND40" is slightly distorted compared to "mosaicEXPAND10" is obvious when considering the case where the fluorescent light of the center wavelength is incident on the optimal phase modulation pattern for only one center wavelength. That is, even if the fluorescent light incident on the phase modulation pattern is the optimal fluorescent light for the phase modulation pattern, the shape of the bright spot image is distorted as the diameter of the incident beam moves away from the diameter of the phase modulation pattern. For this reason, the bright spot image tends to collapse in "mosaicEXPAND40" that has a large amount of deviation in diameter.

FIGS. 28 (e) and 28 (f) show the results of observation of fluorescent light using "mosaicREDUCE20". In this case the two bright spot images were appropriate when observing the first fluorescent light and when observing the second fluorescent light. FIGS. 28 (g) and 28 (h) show the results of observation of fluorescent light using "mosaicREDUCE40". In this case, the two bright spot images were appropriate in the case of observing the first fluorescent light and the case of observing the second fluorescent light, but the bright spot image slightly collapsed as compared with "mosaicREDUCE20". Note that the reason why the bright point image of "mosaicREDUCE40" is slightly distorted compared to "mosaicREDUCE20" is the same reason as the collapse in the case of "mosaicEXPAND40".

Application to Phase Plate Made of Transparent Member

An example in which the phase modulation pattern shown in example 1 is applied to a phase plate made of a transparent member will be described with reference to FIGS. 29 (a) to 29 (f).

Figure 29:
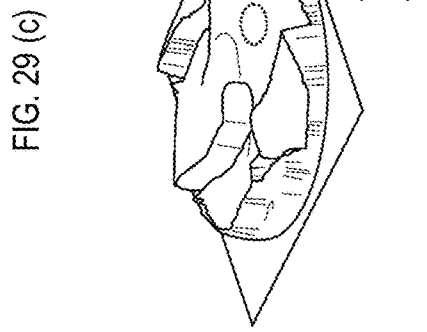
FIG. 29 (a) is a schematic view showing the phase plate manufactured so as to correspond to the first phase modulation pattern of the embodiment.
Figure 29:
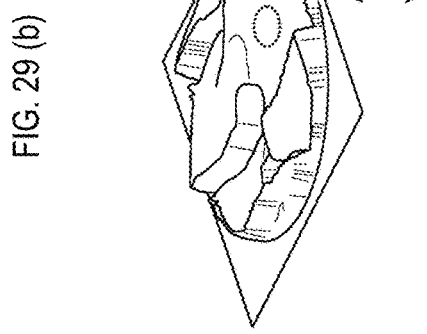
Figure 29:
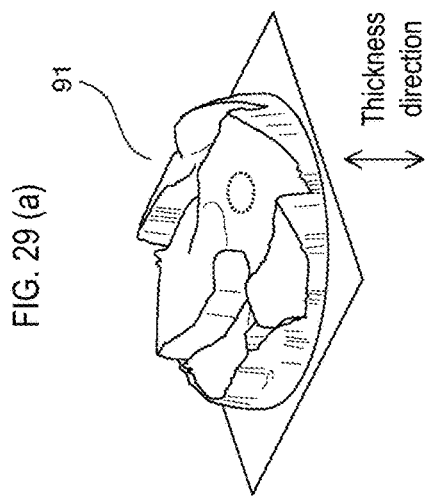
Figure 29:
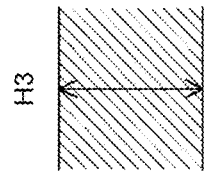
Figure 29:
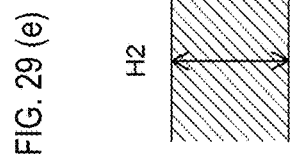
Figure 29:
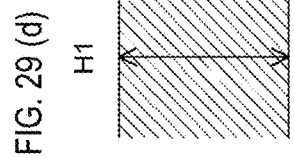

FIG. 29 (a) is a phase plate 91 manufactured so as to correspond to the first phase modulation pattern shown in FIG. 7 (a). FIG. 29 (b) is a phase plate 92 manufactured so as to correspond to the second phase modulation pattern shown in FIG. 7 (b). Phase plates 91 and 92 are made of the same material as phase plate 52. In phase plate 91, a thick portion corresponds to an area near white in the first phase modulation pattern, and a thin portion corresponds to a region close to black in the first phase modulation pattern. In phase plate 92, a thick portion corresponds to an area near white in the second phase modulation pattern, and a thin portion corresponds to a region close to black in the second phase modulation pattern.

The maximum thickness of the phase plate 91 is designed so that the phase of the first fluorescent light entering the maximum thickness portion is shifted by one wavelength. Similarly, the maximum thickness of the phase plate 92 is designed so that the phase of the second fluorescent light entering the maximum thickness portion is shifted by one wavelength. The phase plate 91 imparts a first phase modulation to the light of the first wavelength, that is, the first fluorescent light. The phase plate 92 imparts a second phase modulation to the light of the second wavelength, that is, the second fluorescent light.

The phase plates 91 and 92 are synthesized in the same manner as the phase modulation pattern of example 1 to produce the phase plate 52 as shown in FIG. 29 (c). The thickness of the phase plate 52 has a thickness between the thickness of the phase plate for the light of the first wavelength and the thickness of the phase plate for the light of the second wavelength, that is, the thickness of the phase plate 52 has a thickness between the thickness of the phase plate 91 optimal for the first fluorescent light and the thickness of the phase plate 92 optimal for the second fluorescent light. The phase plate 52 is made of a transparent member such as an acrylic resin. Note that the transparent member configuring the phase plate 52 need not necessarily be transparent, and may be any material as long as it can transmit light.

Note that the thickness T1 of the phase plate 91 and the thickness T2 of the phase plate 92 are calculated by the following equations. In the following equations, n1 is the refractive index around the phase plates 91 and 92, that is, the refractive index of air. N2 is the refractive index of the phase plates 91 and 92, that is, the refractive index of the phase plate 52 to be produced. λ1 is the center wavelength of the first fluorescent light and λ2 is the center wavelength of the second fluorescent light. θ is the phase shift amount.

Thickness $T1 = \lambda 1 \times \theta / \{2\pi(n2 - n1)\}$

Thickness $T2 = \lambda 2 \times \theta / \{2\pi(n2 - n1)\}$

Note that $T2/T1 = \lambda 2/\lambda 1$.

For example, in the phase plates 91 and 92, when the maximum shift amount of the phases of the first fluorescent light and the second fluorescent light is θmax, the thicknesses T1 and T2 obtained by substituting θmax into the above formula correspond to the maximum thickness of phase plates 91 and 92. The thickness of the phase plate 52 is set to a thickness between the maximum thickness of the phase plate 91 and the maximum thickness of the phase plate 92. Similarly, in regions outside the region where the phase plates 91 and 92 have the maximum thickness, the thickness of the phase plate 52 is set to a thickness between the thickness T1 and the thickness T2 obtained based on the phase shift amount.

In the equation for calculating the thickness, when the range of θ is $2(m-1)\pi < \theta \leq 2m\pi$ (where m is a positive integer), the following equation is preferable. In this way it is possible to suppress a decrease in light transmittance.

$$\text{Thickness } T1 = \lambda 1 \{\theta - 2(m-1)\pi\} / \{2\pi(n2-n1)\}$$

$$\text{Thickness } T2 = \lambda 2 \{\theta - 2(m-1)\pi\} \{2\pi(n2-n1)\}$$

FIGS. 29 (d) to 29 (f) are diagrams schematically showing cross sections obtained by sectioning a region surrounded by a dotted line in FIGS. 29 (a) to 29 (c) in planes parallel to the thickness direction. The thickness of the region surrounded by the dotted line is designated a first thickness H1 in the case of the phase plate 91, and a second thickness H2 in the case of the phase plate 9. 2 The first thickness H1 is a thickness for properly forming an image corresponding to the DH-PSF of the first fluorescent light, and the second thickness H2 is a thickness for properly forming an image corresponding to the DH-PSF of the second fluorescent light. Here, the phase plate 52 is manufactured based on the same method as when manufacturing the phase modulation pattern of example 1, and the thickness of the phase plate 52 is distributed with thickness between the thickness of the phase plate 91 and the thickness of the phase plate 92. Therefore, when the thickness of the phase plate 52 in the region surrounded by the dotted line is designated a third thickness H3, the third thickness H3 is calculated by the following equation.

$$\text{Third thickness } H3 = (\text{first thickness } H1 \times a + \text{second thickness } H2 \times b)/(a+b)$$

As in the case where the phase modulation pattern of example 1 is set in the phase modulation device 51, the phase plate 52 manufactured in this manner properly forms the image corresponding to the DH-PSF of both the first fluorescent light and the second fluorescent light. As in the verification results in the phase modulation pattern of example 1, the closer are the value of a and the value of b, the more properly the image corresponding to the DH-PSF of both the first fluorescent light and the second fluorescent light can be formed.

An example in which the phase modulation pattern shown in example 2 is applied to a phase plate made of a transparent member will be described with reference to FIGS. 30 (a) to 30 (i).

The phase plate 91 of FIG. 30 (a) is the same as the phase plate of FIG. 29 (a), and the phase plate 92 of FIG. 30 (b) is the same as the phase plate of FIG. 29 (b). The phase plates 91 and 92 are arranged in a mosaic pattern the same as the phase modulation pattern of example 2 to produce the phase plate 52 as shown in FIG. 30 (c).

As shown by light gray in FIG. 30 (d), the phase plate 91 is fabricated so as to have an optimum thickness only for the first fluorescent light throughout the entire region. As shown by light gray in FIG. 30 (e), the phase plate 92 is fabricated so as to have an optimum thickness only for the second fluorescent light over the entire region. That is, the phase plate 91 is set similarly to the first phase modulation pattern, and the phase plate 92 is set in the same manner as the second phase modulation pattern. As indicated by the mosaic pattern of light gray and dark gray in FIG. 30 (f), the phase plate 52 shown in FIG. 30 (c) has a first region of optimal thickness for the first fluorescent light and a second region of optimal thickness for the second fluorescent light arranged in a mosaic pattern.

In other words, the first region indicated by light gray in FIG. 30 (f) is a region configured to impart the first phase modulation to the light of the first wavelength, that is, the first fluorescent light, in the incident region. The second region indicated by dark gray in FIG. 30 (f) is a region configured to impart the second phase modulation to the light of the second wavelength, that is, the second fluorescent light, in the incident region.

FIGS. 30 (g) to 30 (i) are diagrams schematically showing cross sections obtained by sectioning a region surrounded by a dotted line in FIGS. 30 (d) to 30 (f) in planes parallel to the thickness direction. Hereinafter, for convenience, the value of M in the phase modulation pattern of example 2 is set to 1. The thickness of the four pixel section of the region surrounded by the dotted line is a first thickness H11 to H14 in the case of the phase plate 91, and a second thickness H21 to H24 in the case of the phase plate 92. In this case the thickness of the phase plate 52 becomes, for example, a thickness that alternatingly appears as the thickness of the phase plate 91 and the thickness of the phase plate 92, as shown in FIG. 30 (i).

In other words, the configuration of the phase plate 52 shown in FIG. 30 (i) is as follows. The phase plate 52 includes a first region composed of a light gray region and a second region composed of a dark gray region in the incident region, as shown in FIG. 30 (f). Each region of the first region and each region of the second region are adjacent to each other. The same thickness as that of the phase plate 91 is set in the first region. The same thickness as that of the phase plate 92 is set in the second region. As shown in FIG. 30 (i), the thickness at the position corresponding to the first region is designated the first thickness H11 and H13, and the thickness at the position corresponding to the second region is the second thickness H22 and H24.

As in the case where the phase modulation pattern of example 1 is set in the phase modulation device 51, the phase plate 52 manufactured in this manner properly forms the image corresponding to the DH-PSF of both the first fluorescent light and the second fluorescent light.

Note that although the structural example of the phase modulation mask 50 shown in FIG. 1 has been described in terms of the phase plate 52 made of a transparent member and phase modulation device 51 having a liquid crystal panel 51a, the structure of the phase modulation mask 50 is not limited to this example. For example, the phase modulation mask 50 also may be a deformable mirror provided with minute mirrors that reflect light according to the setting at different positions in the incident direction at each position within the incident surface. Alternatively, the phase modulation mask 50 also may be a reflection member that reflects light at different positions in the incident direction at each position in the incident surface.

What is claimed is:

1. An optical device comprising:
   a phase modulation mask configured to impart phase modulation on both light of a first wavelength and light of a second wavelength;
   an irradiation optical system configured to cause both the light of the first wavelength and the light of the second wavelength to enter the phase modulation mask; and
   a light collecting optical system configured to collect the light of the first wavelength and the light of the second wavelength that have been phased modulated by the phase modulation mask to form images respectively for each light of wavelength, the images varing in response to the modulated phase of the light according to a point spread function; wherein the phase modulation mask is a phase plate; and
the phase plate has a thickness between a thickness of the phase plate for the light of the first wavelength and the thickness of a phase plate for the light of the second wavelength.

2. An optical device comprising:
a phase modulation mask configured to impart phase modulation on both light of a first wavelength and light of a second wavelength;
an irradiation optical system configured to cause both the light of the first wavelength and the light of the second wavelength to enter the phase modulation mask; and
a light collecting optical system configured to collect the light of the first wavelength and the light of the second wavelength that have been phased modulated by the phase modulation mask to form images respectively for each light of wavelength, the images varing in response to the modulated phase of the light according to a point spread function; wherein
the phase modulation mask is a phase modulation device capable of setting a phase modulation pattern based on an input; and
the phase modulation device imparts phase modulation to both the light of the first wavelength and the light of the second wavelength by a phase modulation pattern set based on an input gradient between the gradient of the light of the first wavelength and the gradient of the light of the second wavelength.

3. The optical device of claim 1, wherein
the phase modulation mask is a phase plate; and
the phase plate comprises a first region configured to apply the first phase modulation to light of the first wavelength, and a second region configured to apply the second phase modulation to light of the second wavelength in an incidence area.

4. The optical device of claim 1, wherein
the phase modulation mask is a phase modulation device capable of setting a phase modulation pattern based on an input; and
the phase modulation pattern comprises a first region configured to apply the first phase modulation to light of the first wavelength, and apply the second phase modulation to light of the second wavelength in an incidence area.

5. The optical device of claim 3, wherein
the first region and second region are comprised by a plurality of areas, and
each area of the first region and each area of the second region are adjacent to each other.

6. The imaging device of claim 5, wherein
each area of the first region and each area of the second region are rectangular.

7. The imaging device of claim 6, wherein
each area of the first region and each area of the second region extend from one end of an incidence region to other end.

8. The imaging device of claim 5, wherein
each area of the first region and each area of the second region are ring shaped.

9. The optical device of claim 1, wherein
the light of the first wavelength and the light of the second wavelength is a first fluorescent light and a second fluorescent light given off from a fluorescent substance.

10. The optical device of claim 9, wherein
the wavelength band of the first fluorescence and the wavelength band of the second fluorescence each have a spread and a part of the wavelength band of the first fluorescence and a part of the wavelength band of the second fluorescence overlap each other.

11. The optical device of claim 1, wherein
the light of the first wavelength is light having a peak intensity at the first wavelength, and
the light of the second wavelength is light having a peak intensity at the second wavelength.

12. The optical device of claim 1, wherein
the irradiation optical system comprises an objective lens;
the phase modulation mask images bright spots of the light of the first wavelength and the bright spots of the light of the second wavelength at two points on the imaging plane, that is, modulates the phases of the first fluorescent light and the second fluorescent light so as to form a point spread function in which two bright spot images of the light of the first wavelength and two bright spot images of the light of the second wavelength rotate on the imaging plane according to the distance between the objective lens and the bright spot of the light of the first wave length and the bright spot of the light of the second wavelength.

13. The optical device of claim 1, wherein
the light collecting optical system comprises an imaging part that captures the image of the light of the first wavelength and the image of the light of the second wavelength.

14. The optical device of claim 13, further comprising:
a stage for placing a sample;
wherein the irradiation optical system irradiates light emitted from a light source part on the sample; and
the light collecting optical system collects light of the first wavelength and light of the second wavelength given off from the substances contained in the sample.

15. The optical device of claim 14, wherein
the sample contains a first fluorescent dye and a second fluorescent dye;
the light source part configured to irradiate light on the sample so that the active state and the inactive state are repeated in the first fluorescent dye and the second fluorescent dye; and
the imaging part configured to capture the image of the light of the first wavelength given off from the first fluorescent substance and the image of the light of the second wavelength given off from the second fluorescent substance while the first fluorescent substance and the second fluorescent substance repeat an active state and an inactive state.

* * * * *